(12) United States Patent
Cuadros et al.

(10) Patent No.: US 10,987,071 B2
(45) Date of Patent: Apr. 27, 2021

(54) PIXELATED K-EDGE CODED APERTURE SYSTEM FOR COMPRESSIVE SPECTRAL X-RAY IMAGING

(71) Applicants: Angela Cuadros, Newark, DE (US); Gonzalo Arce, Newark, DE (US)

(72) Inventors: Angela Cuadros, Newark, DE (US); Gonzalo Arce, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 16/624,692

(22) PCT Filed: Jun. 29, 2018

(86) PCT No.: PCT/US2018/040310
§ 371 (c)(1),
(2) Date: Dec. 19, 2019

(87) PCT Pub. No.: WO2019/006310
PCT Pub. Date: Jan. 3, 2019

(65) Prior Publication Data
US 2020/0121269 A1 Apr. 23, 2020

Related U.S. Application Data

(60) Provisional application No. 62/526,389, filed on Jun. 29, 2017.

(51) Int. Cl.
*G01T 1/36* (2006.01)
*A61B 6/00* (2006.01)
(Continued)

(52) U.S. Cl.
CPC ............ *A61B 6/4042* (2013.01); *A61B 6/025* (2013.01); *A61B 6/03* (2013.01); *A61B 6/032* (2013.01);
(Continued)

(58) Field of Classification Search
CPC ....... A61B 6/4042; A61B 6/025; A61B 6/032; A61B 6/04; A61B 6/482; A61B 6/4078; A61B 6/4085; G01T 1/36
See application file for complete search history.

(56) References Cited

U.S. PATENT DOCUMENTS 4,360,797 A * 11/1982 Fenimore ................ G01T 1/295
250/363.06
5,602,893 A * 2/1997 Harding .................... G01T 1/29
378/147
(Continued)

OTHER PUBLICATIONS

International Search Report and Written Opinion for International Application No. PCTUS/2018/04031 , 7 pages.
(Continued)

*Primary Examiner* — David P Porta
*Assistant Examiner* — Djura Malevic
(74) *Attorney, Agent, or Firm* — RatnerPrestia

(57) ABSTRACT

Aspects of the invention are directed to systems and methods for generating spectral computed tomography data for spectral X-ray image reconstruction using of pixelated k-edge apertures. A method is provided for generating a spectral computed tomography. The method includes the steps of generating a plurality of X-ray beams; encoding the plurality of X-ray beams by transmitting the plurality of beams through a pixelated K-edge coded aperture structure; detecting the encoded plurality of X-ray beams; and reconstructing a spectral CT image from the encoded plurality of X-ray beams.

26 Claims, 21 Drawing Sheets

(51) Int. Cl.
  *A61B 6/03* (2006.01)
  *A61B 6/02* (2006.01)
  *A61B 6/04* (2006.01)
  *G06T 11/00* (2006.01)

(52) U.S. Cl.
  CPC .............. *A61B 6/04* (2013.01); *A61B 6/482* (2013.01); *G01T 1/36* (2013.01); *A61B 6/4078* (2013.01); *A61B 6/4085* (2013.01); *G06T 11/006* (2013.01); *G06T 2211/436* (2013.01)

(56) References Cited

U.S. PATENT DOCUMENTS

| | | | | |
|---|---|---|---|---|
| 5,940,468 | A * | 8/1999 | Huang | G01T 1/295 378/57 |
| 6,737,652 | B2 * | 5/2004 | Lanza | G01T 1/295 250/237 R |
| 7,283,231 | B2 * | 10/2007 | Brady | G06T 9/00 356/303 |
| 7,583,783 | B2 * | 9/2009 | Harding | G01N 23/046 378/4 |
| 7,623,614 | B2 * | 11/2009 | Shefsky | G01N 23/02 378/2 |
| 7,888,626 | B2 * | 2/2011 | Slinger | G06T 1/0007 250/226 |
| 7,912,173 | B2 * | 3/2011 | Brady | G06T 11/005 378/2 |
| 7,915,590 | B2 * | 3/2011 | Starfield | G01T 1/295 250/363.02 |
| 7,949,101 | B2 * | 5/2011 | Morton | G01N 23/087 378/124 |
| 8,135,110 | B2 * | 3/2012 | Morton | G01V 5/0016 378/57 |
| 8,149,400 | B2 * | 4/2012 | Brady | G01J 3/2823 356/326 |
| 8,223,919 | B2 * | 7/2012 | Morton | G01N 23/046 378/57 |
| 8,320,519 | B2 * | 11/2012 | Ribbing | G01T 1/2985 378/9 |
| 8,558,182 | B2 * | 10/2013 | Chi | H04N 5/2254 250/363.06 |
| 8,837,669 | B2 * | 9/2014 | Morton | A61B 6/022 378/41 |
| 9,040,930 | B2 * | 5/2015 | Kyele | G01T 1/2914 250/370.1 |
| 9,110,172 | B2 * | 8/2015 | Lalleman | G01T 1/295 |
| 9,113,839 | B2 * | 8/2015 | Morton | G01N 23/04 |
| 9,335,281 | B2 * | 5/2016 | Marks | G01N 23/20008 |
| 9,490,099 | B2 * | 11/2016 | Mackie | A61B 6/06 |
| 10,004,464 | B2 * | 6/2018 | Brady | A61B 6/032 |
| 10,045,752 | B2 * | 8/2018 | Gupta | A61B 6/4007 |
| 10,055,859 | B2 * | 8/2018 | Proksa | A61B 6/032 |
| 10,107,768 | B2 * | 10/2018 | Brady | G01N 23/20008 |
| 10,151,629 | B2 * | 12/2018 | Lau | G01J 3/108 |
| 10,228,283 | B2 * | 3/2019 | Nath | G01J 3/0208 |
| 10,261,212 | B2 * | 4/2019 | Schafer | G01V 5/0066 |
| 10,423,002 | B2 * | 9/2019 | Shimano | G02B 27/4205 |
| 10,488,535 | B2 * | 11/2019 | Perlman | H04N 5/2254 |
| 10,755,135 | B2 * | 8/2020 | Xavier da Silveira | G06K 9/209 |
| 10,768,125 | B2 * | 9/2020 | Kato | G01N 23/223 |
| 10,874,361 | B2 * | 12/2020 | Cuadros | A61B 6/025 |
| 2002/0075990 | A1 * | 6/2002 | Lanza | G01T 1/295 378/2 |
| 2003/0152290 | A1 * | 8/2003 | Odell | G01S 3/7835 382/291 |
| 2006/0023832 | A1 * | 2/2006 | Edie | A61B 6/4028 378/7 |
| 2006/0274308 | A1 * | 12/2006 | Brady | G01J 3/2803 356/326 |
| 2007/0253525 | A1 * | 11/2007 | Popescu | A61B 6/5282 378/7 |
| 2007/0263914 | A1 * | 11/2007 | Tibbetts | G01J 3/2846 382/129 |
| 2008/0128625 | A1 * | 6/2008 | Lamadie | G01T 1/295 250/361 R |
| 2009/0020714 | A1 * | 1/2009 | Slinger | G01T 1/295 250/550 |
| 2009/0022410 | A1 * | 1/2009 | Haskell | G01T 1/295 382/238 |
| 2009/0040516 | A1 * | 2/2009 | Fritz | G01J 3/4412 356/301 |
| 2009/0090868 | A1 * | 4/2009 | Payne | G01T 1/295 250/363.06 |
| 2009/0095912 | A1 * | 4/2009 | Slinger | G06T 1/0007 250/363.06 |
| 2009/0116612 | A1 * | 5/2009 | Ziegler | A61B 6/4014 378/9 |
| 2009/0167922 | A1 * | 7/2009 | Perlman | H04N 5/22541 348/340 |
| 2009/0207968 | A1 * | 8/2009 | Grass | A61B 6/032 378/9 |
| 2009/0279659 | A1 * | 11/2009 | David | A61B 6/032 378/7 |
| 2011/0019068 | A1 * | 1/2011 | Chiu | H04N 5/23212 348/349 |
| 2012/0027173 | A1 * | 2/2012 | Duerr | H01J 1/304 378/62 |
| 2013/0051521 | A1 * | 2/2013 | Basu | G01N 23/087 378/53 |
| 2013/0234029 | A1 * | 9/2013 | Bikumandla | H01L 27/1464 250/349 |
| 2014/0247920 | A1 * | 9/2014 | Marks | G01N 23/207 378/87 |
| 2015/0028763 | A1 * | 1/2015 | Feri | H05B 45/40 315/210 |
| 2018/0080822 | A1 * | 3/2018 | Lau | G01J 3/0229 |

OTHER PUBLICATIONS

Cuadros et al., "Coded Aperture Compressive X-ray Spectral CT", 2017 International Conference on Sampling Theory and Applications, 2017, pp. 548-551.

Rakvonghtai et al., "Spectral CT Using Multiple Balanced K-Edge Filters", IEEE Transactions on Medical Imaging, Mar. 2015, vol. 34, No. 3, pp. 740-747.

Roessl et al., "K-Edge Imaging in X-Ray Computed Tomography Using Multi-Bin Photon Counting Detectors", Physics in Medicine and Biology, 2007, vol. 52, pp. 4679-4696.

International Preliminary Report on Patentability and Written Opinion for International Application No. PCT/US2018/040310, dated Dec. 31, 2019, 7 pages.

Notice of Allowance for U.S. Appl. No. 16/215,805, dated Sep. 25, 2020, 10 pages.

* cited by examiner

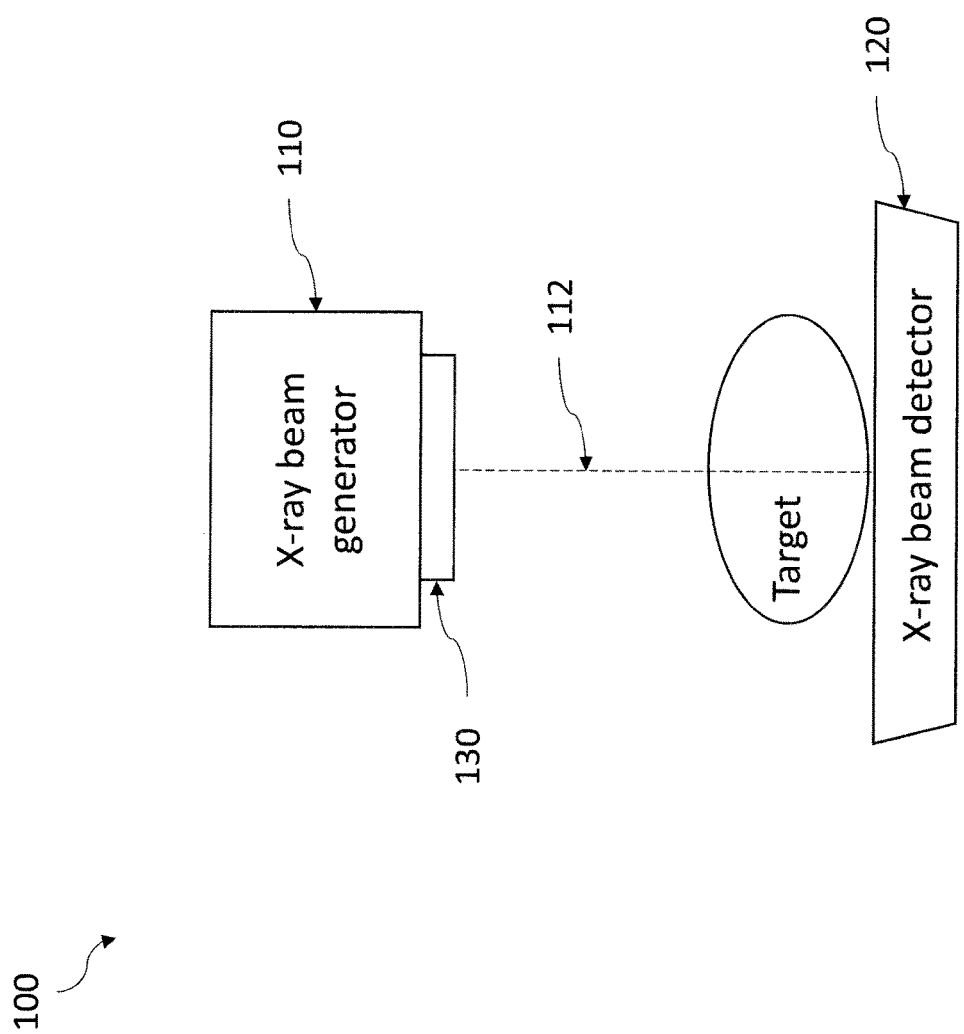

US 10,987,071 B2

PIXELATED K-EDGE CODED APERTURE SYSTEM FOR COMPRESSIVE SPECTRAL X-RAY IMAGING

CROSS-REFERENCE TO RELATED APPLICATION

This application claims priority benefit of a national stage application under 35 U.S.C. 371 of International Application No. PCT/US2018/040310, filed Jun. 29, 2018, which is related to and claims priority to U.S. Provisional Application No. 62/526,389 entitled "Pixelated K-Edge Coded Aperture System for Compressive Spectral X-Ray Imaging" filed on Jun. 29, 2017, the disclosures of each of these applications being incorporated herein by reference in their entireties for all purposes.

FIELD OF THE INVENTION

Aspects of the invention are directed to systems and methods for generating spectral computed tomography data for X-ray spectral image reconstruction using a pixelated K-edge coded aperture structure.

BACKGROUND

X-ray computed tomography (hereafter "CT") has become an important tool in medical diagnosis. Tomographic gray scale images obtained from conventional systems, however, are often insufficient to reveal differences between materials having different chemical compositions but the same X-ray attenuation coefficients. Spectral Computed Tomography (hereafter "SCT") not only provides morphological information, as conventional CT scans do, but it also allows material decomposition as well. Thus, the emerging field of SCT has important application in medical imaging and transit security.

On the other hand, higher energy resolution can be achieved by using photon counting detectors, which can identify the energy of incoming photons and record the data in the corresponding energy bins. The advantages of spectral tomography, however, are hindered by several technical challenges that prevent their broad practical application, such as costly photon counting detectors and their low signal to noise ratio. In addition, traditional methods for spectral X-ray CT imaging are time intensive as they use multiple scans when employing standard integrating detectors.

Accordingly, there is a need for improved methods and system for generating spectral computed tomography data.

SUMMARY OF THE INVENTION

Aspects of the invention are directed to systems and methods for generating spectral computed tomography data for X-ray spectral image reconstruction using a pixelated K-edge coded aperture structure.

According to one aspect of the invention, a method is provided for generating spectral computed tomography data. The method includes the steps of generating a plurality of X-ray beams; encoding the plurality of X-ray beams by transmitting the plurality of beams through a pixelated K-edge coded aperture structure; detecting the encoded plurality of X-ray beams; and reconstructing a spectral CT image from the encoded plurality of X-ray beams.

In accordance with a further aspect of the invention, another method is provided for generating spectral X-ray tomography data. The method includes the steps of scanning a target with a plurality of X-ray beams during at least one pass of an X-ray beam generator with respect to a target and encoding the plurality of X-ray beams during the at least one pass by transmitting the plurality of X-ray beams through a pixelated K-edge coded aperture structure. The pixelated K-edge coded aperture structure delineates a plurality of openings. The method further includes the steps of detecting an intensity of the encoded plurality of X-ray beams from the at least one pass and reconstructing a spectral CT image of the target from the encoded plurality of X-ray beams.

According to another aspect of the invention, a system employing a pixelated K-edge coded aperture structure is provided for generating spectral computed tomography data. The system includes at least one X-ray generator configured for producing a plurality of X-ray beams and at least one pixelated K-edge coded aperture structures delineating a plurality of openings. The plurality of openings are associated with at least one K-edge filter, such that the difference of the spectra of the plurality of X-ray beams transmitted through the plurality of openings has an energy band corresponding to a difference between K-edge values of a corresponding balanced pair of K-edge filters. The system also includes at least one detector configured to detect the plurality of X-ray beams transmitted through the at least one pixelated K-edge coded aperture structure.

BRIEF DESCRIPTION OF THE DRAWINGS

The invention is best understood from the following detailed description when read in connection with the accompanying drawings, with like elements having the same reference numerals. It is emphasized that according to common practice the various features of the drawings are not drawn to scale unless otherwise indicated. On the contrary, the dimensions of the various features may be expanded or reduced for clarity. Included in the drawings are the following figures.

FIG. 1 is a schematic depicting a system employing pixelated k-edge apertures for generating a spectral computed tomography in accordance with aspects of the invention;

DETAILED DESCRIPTION OF THE INVENTION

Figure 2B:
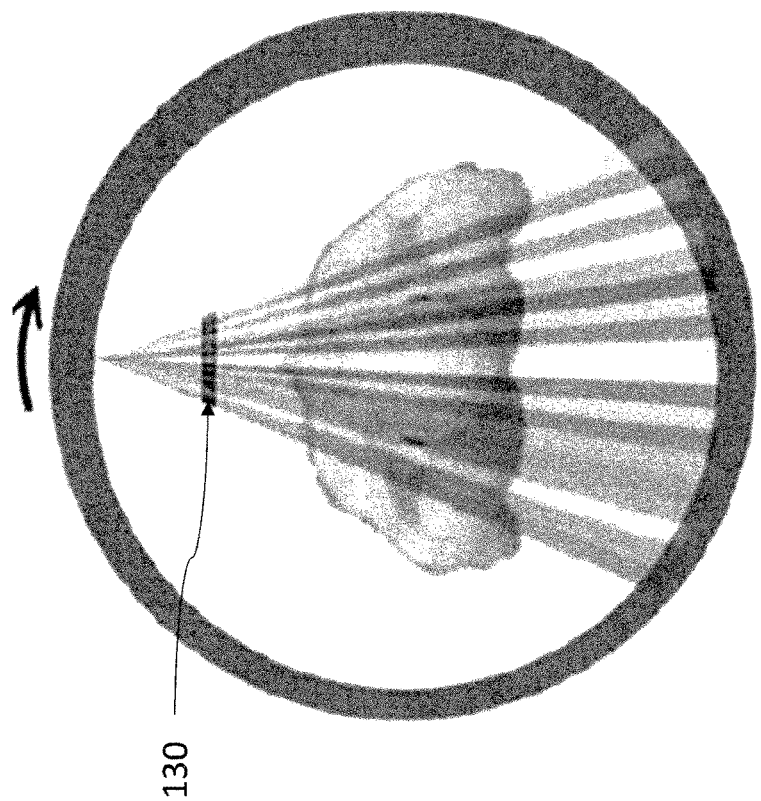
FIG. 2B is a schematic depicting a system using the pixelated K-edge coded aperture mask of FIG. 2A.

Aspects of the invention are directed to systems and methods generating spectral computed tomography data using pixelated K-edge coded aperture structures. Advantageously, embodiments of the invention may overcome many of the limitations of conventional methods used for SCT. In addition, by using pixelated K-edge coded aperture structures, lower-dose structured X-ray bundles that interrogate specific pixels of the target may be created. In one embodiment, advantageously, structured illumination may be used to reduce the number of angles by source multiplexing in limited angle geometries.

A pixelated K-edge coded aperture structure as referred to herein is a structure that has a filtering aspect and a pixelated coding aspect. In one embodiment, the filtering aspect and the pixelated coding aspect are performed by a single structure including a plurality of apertures having at least one K-edge filter incorporated therein. In another embodiment, the pixelated K-edge coded aperture structure includes a first structure (e.g., patterned structure) for pixelating the X-ray beam(s) and a second structure (e.g., K-edge filter structure) for filtering of the X-ray beam(s) that is separate from the first structure.

FIG. 1 depicts a spectral CT imaging system 100 employing pixelated k-edge apertures for generating spectral computed tomography data in accordance with aspects of the invention. As a general overview, spectral CT imaging system 100 includes an X-ray generator 110, an X-ray beam detector 120, and a pixelated k-edge aperture structure 130.

X-ray beam generator 110 is configured for producing a plurality of X-ray beams 112 for imaging a target. Suitable X-ray beam generators 110 include those configured to produce monochromatic and/or polychromatic X-ray beams 112. X-ray beam generator 110 may be configured to produce and/or deliver X-ray beams 112 in the form of cone beams, fan beams, or any other suitable forms for producing and/or delivering X-ray beams 112. X-ray beam generator 110 may be coupled to a gantry configured for positioning X-ray beam generator 110 relative to the target and/or X-ray beam detector 120. One of ordinary skill in the art would readily recognize suitable gantries for positioning X-ray beam generator 110 relative to the target and/or X-ray beam detector 120. Additionally and/or alternatively, the target may reside on a patient positioning system that is configured to position and/or rotate the patient relative to the X-ray beam generator 110 and/or X-ray beam detector 120. Suitable patient positioning systems would be known to one of ordinary skill in the art.

X-ray beam detector 120 is configured to detect and/or sense X-ray beams 112 produced by X-ray beam generator 110. X-ray beam detector 120, preferably, has a geometry corresponding to X-ray beams 112 generator by x-ray beam generator 110. For example, X-ray beam detector 120 may be a line detector that is adapted for detecting a X-ray fan beam 112 produced by X-ray beam generator 110. In another example, X-ray beam detector 120 may be a two dimensional detector that is adapted for detecting an X-ray cone beam 112 produced by an X-ray beam generator 120.

Figure 2A:
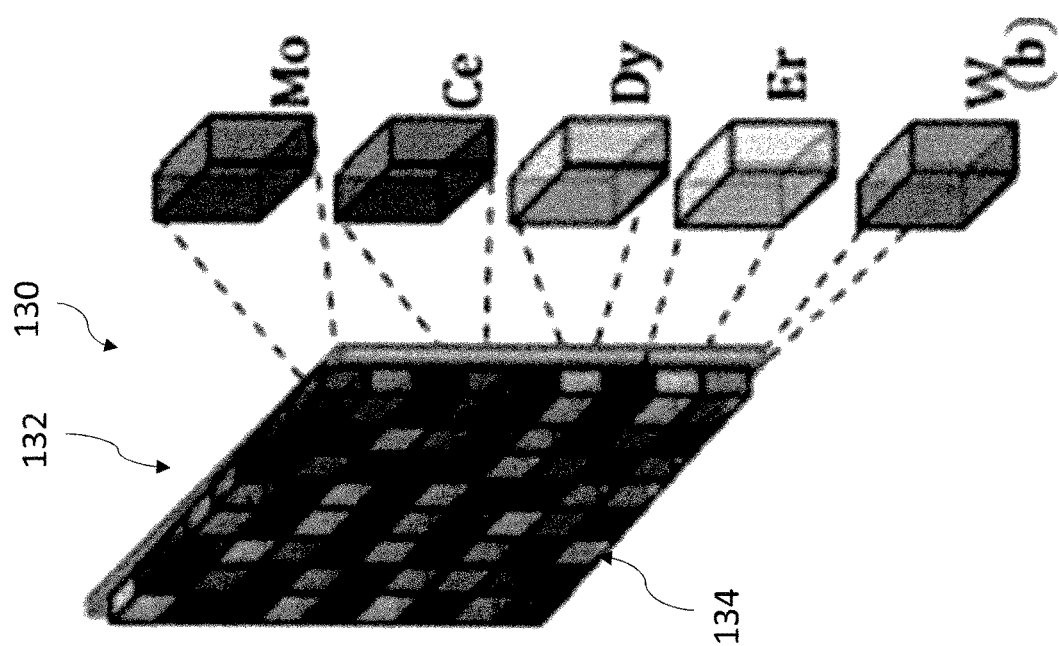
FIG. 2A is a schematic depicting a pixelated K-edge coded structure formed from a single structure having a plurality of openings according to aspects of the invention.
Figure 2C:
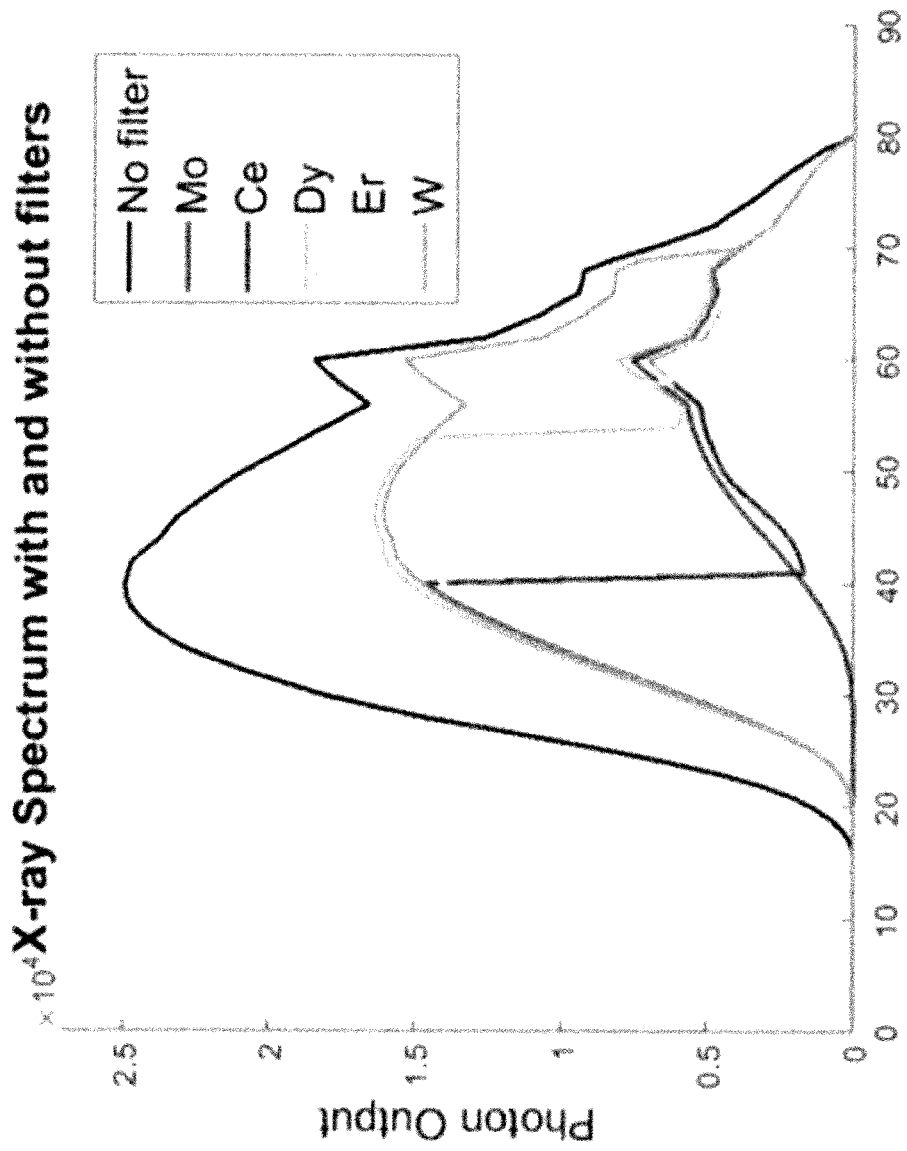
FIG. 2C is a graph of the filtered spectra produced using the system of FIG. 2B with a particular set of Ross filters.

As mentioned above, pixelated K-edge coded aperture structure 130 is a structure that has a filtering aspect and a pixelating aspect. The pixelating aspect and the filtering aspect may be performed by a single structure or by two or more structures. As shown in FIG. 2A, pixelated K-edge coded aperture structure 130 may be a single structure 132 delineating a plurality of openings 134 (e.g., apertures) associated with at least two K-edge filters, where any individual opening of the plurality of opening 134 may contain a single filtering material. For example, each of the plurality of openings 134 may contain at least one K-edge filter incorporated therein. A pair of balanced K-edge filters may be formed by a pair of K-edge filters contained within a corresponding pair of the plurality of openings 134 delineated by single structure 132, i.e., pixelated K-edge coded aperture structure 130.

Additionally and/or alternatively, each of the openings 134 of the pixelated K-edge coded aperture structure 130 is arranged with respect to the other openings 134 to spatially encode the plurality of X-ray beams transmitted through the plurality of openings 134 of pixelated K-edge coded aperture structure 130. For example, each of the plurality of openings 134 may be arranged to form a pattern, such that X-ray beams 112 transmitted through the pixelated K-edge coded aperture structure 130 are encoded to form a pattern. In one embodiment, the plurality of openings 134 are arranged in a randomized pattern, such that the X-ray beams 112 transmitted through pixelated K-edge coded aperture structure 130 are encoded with a randomized pattern. In another embodiment, plurality of openings 134 are arranged in a non-randomized pattern, such that the X-ray beams 112 transmitted through pixelated K-edge coded aperture structure 130 are encoded with a non-randomized pattern that may be optimized to improve spectral CT imaging.

Figure 2D:
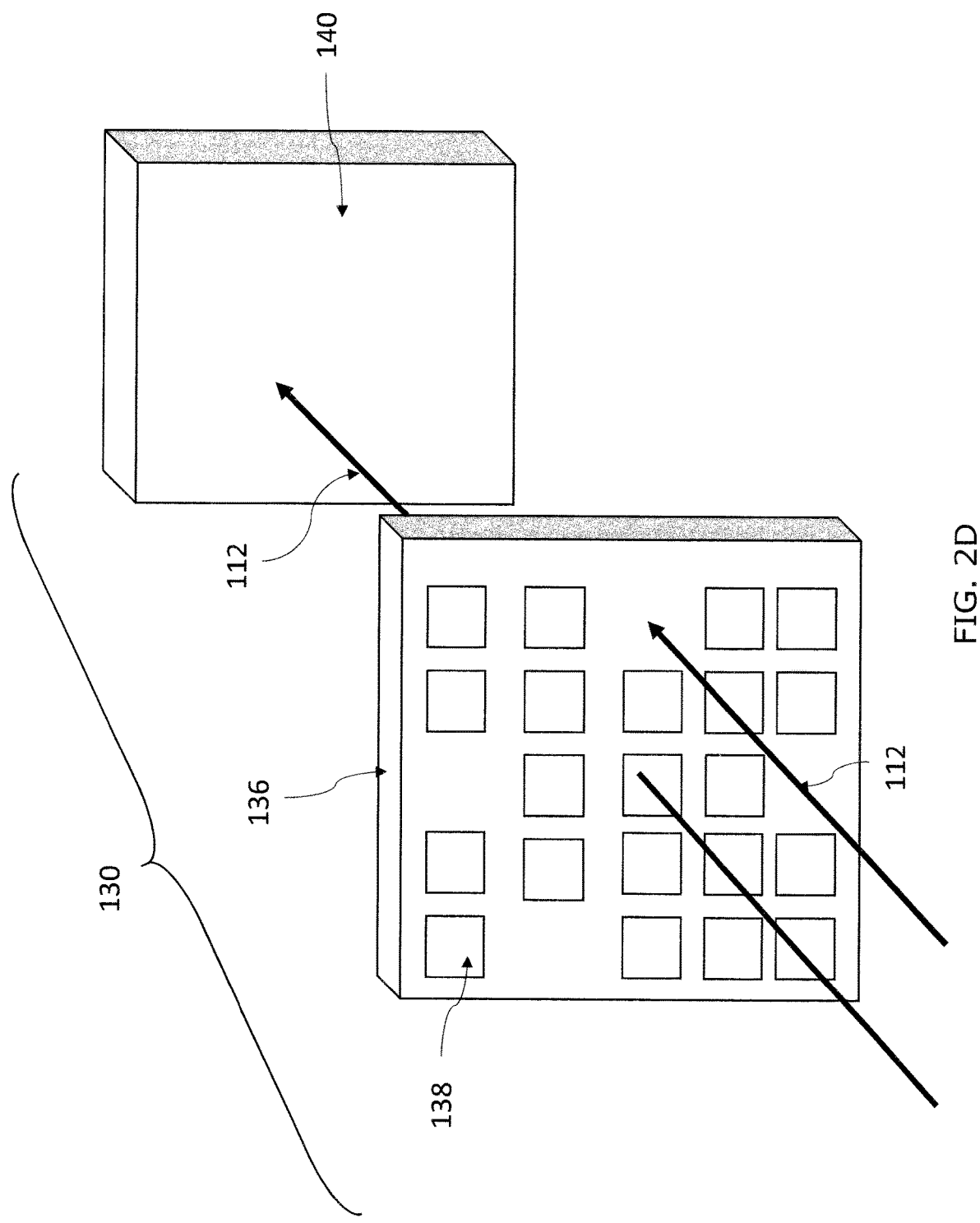
FIG. 2D is a schematic depicting a pixelated K-edge coded structure formed from a first structure for pixelating the X-ray beams and a second structure for filtering the X-ray beams that is separate from the first structure according to aspects of the invention.

In another embodiment, pixelated K-edge coded aperture structure 130 includes a first structure 136 (e.g., patterned structure) for pixelating the plurality of X-ray beams 112 and a second structure 140 (e.g., K-edge filter structure) for filtering of the plurality of X-ray beams that is separate from the first structure 136. As illustrated by the embodiment shown in FIG. 2D, first structure 136 for pixelating X-ray beams 112 may be a block/unblock structure that includes a plurality of openings 138 (e.g., apertures). The block/unblock first structure 136 may be formed of materials, such that X-ray beams 112 contacting the block/unblock first structure 136 are blocked and/or prevented from passing through block/unblock first structure 136 while X-ray beams 112 transmitted through the plurality of openings 138 are permitted to passing through block/unblock first structure 136. As mentioned above, the plurality of openings 138 may be arranged in a pattern such that X-ray beams 112 transmitted through pixelated K-edge coded aperture structure 130 are encoded to form a pattern. The plurality of openings 138 may be arranged in a randomized pattern to encode the X-ray beams 112 transmitted through the pixelated K-edge coded aperture structure 130 with a randomized pattern or arranged in a non-randomized pattern to encode the X-ray beams 112 transmitted through pixelated K-edge coded aperture structure 130 with non-randomized pattern. Although FIG. 2D illustrates a single K-edge filter for second structure 140, a different K-edge filter may be used for second structure 140 in another scanning position.

Pixelated K-edge aperture structure 130 is configured to filter the plurality of X-ray beams 112 using at least two K-edge filters that form at least one pair of K-edge filters. Preferably, the pair of K-edge filters are a balanced pair of K-edge filters. Additionally and/or alternatively, pixelated K-edge aperture structure 130 is configured such that the difference of the spectra of the plurality of X-ray beams transmitted through the plurality of openings has an energy band corresponding to a difference between K-edge values of a corresponding balanced pair of K-edge filters. In one embodiment, at least one pair of K-edge filters are formed of two materials having a difference in atomic number is 16 or less. In another embodiment, at least one pair of K-edge filters are formed of two materials having a difference in atomic number is 16 or more. The K-edge filters may form a Ross filter.

More generally, a K-edge filter is a material consisting of a high-Z element, which is an element with a high atomic number, such as tantalum, tungsten, or molybdenum, which sharply cuts off part of the X-ray spectrum above the element's K-shell electrons' binding energy. By using different K-edge filters in sequential scans, mono-energetic X-ray flux measurements can be obtained and used to reconstruct the linear attenuation coefficients of a particular energy bin. This scheme overcomes the limitations of photon counting detectors. By subtracting the X-ray spectrum acquired from X-ray beams(s) transmitted through the first K-edge filter from the spectrum acquired from X-ray beams(s) transmitted through the second K-edge filter of the pair of K-edge filters, a quasi-monochromatic curve may be obtained at the energy bin between the K-edges of the pair of K-edge filters.

Figure 3:
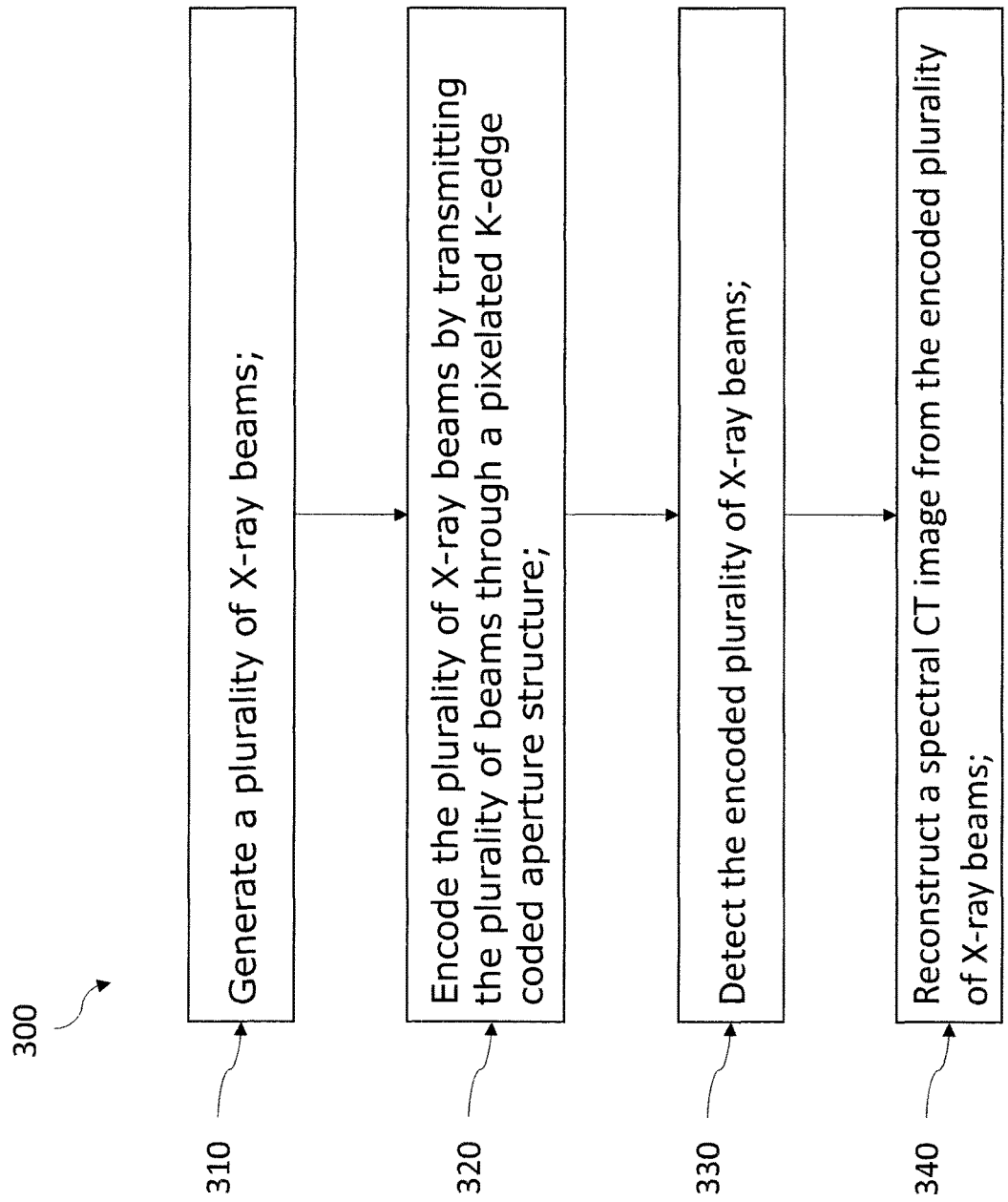
FIG. 3 is a method of generating spectral computed tomography data in accordance with aspects of the invention.

FIG. 3 depicts a method 300 of generating spectral computed tomography data in accordance with aspects of the invention. As a general overview, method 300 includes generating a plurality of X-ray beams; encoding the plurality of X-ray beams by transmitting the plurality of beams through a pixelated K-edge coded aperture structure; detecting the encoded plurality of X-ray beams; and reconstructing a spectral CT image from the encoded plurality of X-ray beams.

In step 310, a plurality of X-ray beams 112 are generated, e.g., using X-ray generators 110 discussed herein. The target may be scanned with the plurality of X-ray beams 112 during at least one pass of an X-ray beam generator with respect to a target. In one embodiment, the target is scanned during a first pass of the X-ray generator 110 relative to the target and scanned during a second pass of the X-ray generator 110 relative to the target. In another embodiment, however, the target is scanned solely during a single pass of the X-ray generator 110 relative to the target. The plurality of X-ray beams 112 may be generated during step 310 may be monochromatic and/or polychromatic X-ray beams 112. Additionally, the plurality of X-ray beams 112 may be delivered to the target in the form of cone beams, fan beams, parallel beams, or any other suitable form for producing and/or delivering X-ray beams 112.

In step 320, the plurality of X-ray beams 112 are encoded by transmitting the plurality of beams through a pixelated K-edge coded aperture structure 130. The plurality of X-ray beams 112 may form a random or non-random pattern after being encoded by way of transmission of the plurality of X-ray beams 112 through the pixelated K-edge coded aperture structure 130. For example, in an embodiment utilizing at least two passes, a first set of X-ray beams 112 are encoded during a first pass of the X-ray generator 110 relative to the target as the first set of X-ray beams 112 is transmitted through pixelated K-edge aperture structure 130 and a second set of X-ray beams 112 are encoded during a second pass of the X-ray generator 110 relative to the target as the second set of X-ray beams 112 is transmitted through pixelated K-edge aperture structure 130. In the embodiment utilizing solely a single pass, the plurality of X-ray beams 112 are encoded during the single pass of the X-ray generator 110 relative to the target.

In step 330, the encoded plurality of X-ray beams 112 are detected, e.g., using X-ray beam detector 120 discussed herein. X-ray beam detector 120 may detect an intensity of the encoded plurality of X-ray beams 112. For example, X-ray beam detector 120 may detect a first intensity of encoded X-ray beams 112 transmitted through a first K-edge filter and detect a second intensity of encoded X-ray beams 112 transmitted through a second K-edge filter. Although not illustrated, method 300 may include the step of determining the quasi-monochromatic intensities associated with the encoded X-ray beams 112, e.g., by subtracting the first intensity of the encoded X-ray beams 112 associated with a first K-edge filter from a second intensity of the encoded X-ray beams associated with a second K-edge filter. The determination of the quasi-monochromatic intensities by the subtraction of the first intensity of the encoded X-ray beams 112 associated with a first K-edge filter from a second intensity of the encoded X-ray beams associated with a second K-edge filter is just one example, other procedures may be employed to determine the quasi-monochromatic intensities associated with the encoded X-ray beams 112.

In step 340, a spectral CT image is reconstructed from the encoded plurality of X-ray beams 112. Reconstruction algorithms, such as those discussed herein, may be employed to facilitate reconstruction of the spectral CT image from the detected plurality of X-ray beams 112. In one embodiment, the spectral CT image of the target is reconstructed using quasi-monochromatic intensity measurements, e.g., by solving an inverse problem.

Figure 4:
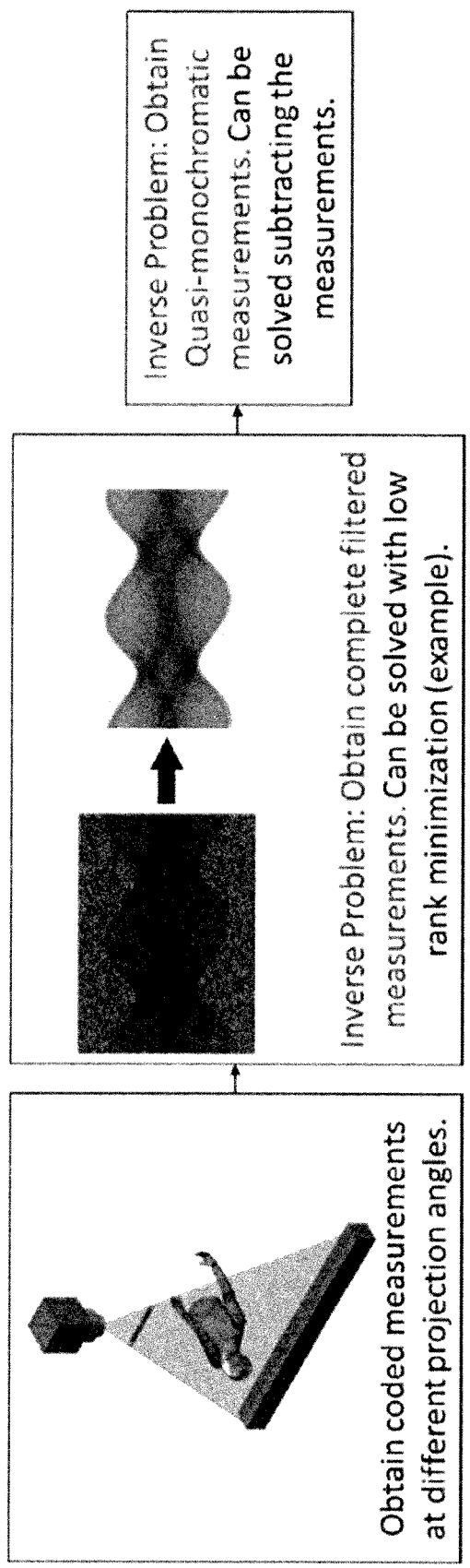
FIG. 4 is a schematic depicting exemplary steps for obtaining spectral CT images according to aspects of the invention.

FIG. 4 is a schematic depicting non-limiting, exemplary steps for obtaining spectral CT images. The detected encoded plurality of X-ray beams 112 may be used to obtain the quasi-monochromatic measurements by solving an inverse problem. For example, low-rank minimization may be used to obtain complete filtered sinograms, which may be subtracted by pairs as in the embodiment utilizing multiple shots of X-ray beams 112 and/or two or more passes of X-ray generator 110 relative to the target. By way of another example, sparsity promoting algorithms may be used to reconstruct CT images from the detected encoded plurality of X-ray beams 112 and, subsequently, using these images to obtain the complete filtered sinograms. These sinograms are then used to obtain the quasi-monochromatic measurements by solving a least squares problem; subtracting the complete measurements is another alternative to obtain the quasi-monochromatic measurements. In both of the above procedures, conventional CT algorithms, algebraic reconstruction methods or sparsity promoting algorithms can be used to reconstruct the spectral CT images.

Figure 5:
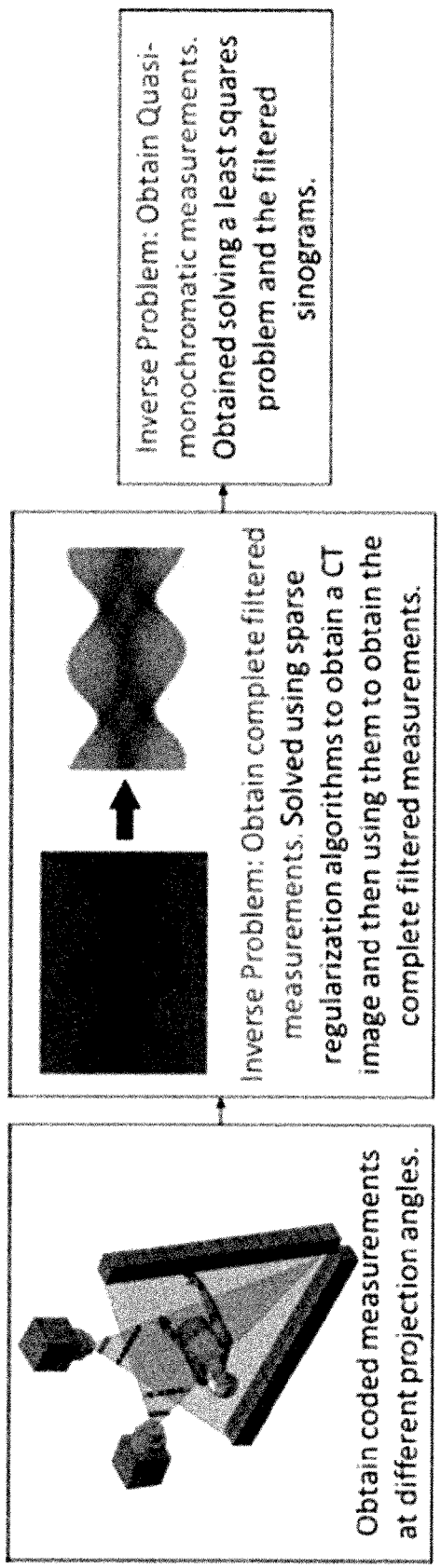
FIG. 5 is a schematic depicting further non-limiting, exemplary steps for obtaining spectral CT images in accordance with aspects of the invention.

FIG. 5 is a schematic depicting further non-limiting, exemplary steps for obtaining spectral CT images. In order to filter the plurality of X-ray beams 112, a K-edge filter from a balanced pair may be used in each projection angle and a block/unblock coded pattern first structure 136 may be positioned before or after the second filter structure 140. Thus, the obtained measurements in each angle may be obtained having a single K-edge filtered X-ray projection with an illumination pattern provided by the block/unblock coded pattern first structure 136. Sinograms may be used to obtain the quasi-monochromatic measurements and, ultimately, reconstruct the spectral CT images as further discussed herein.

Figure 6:
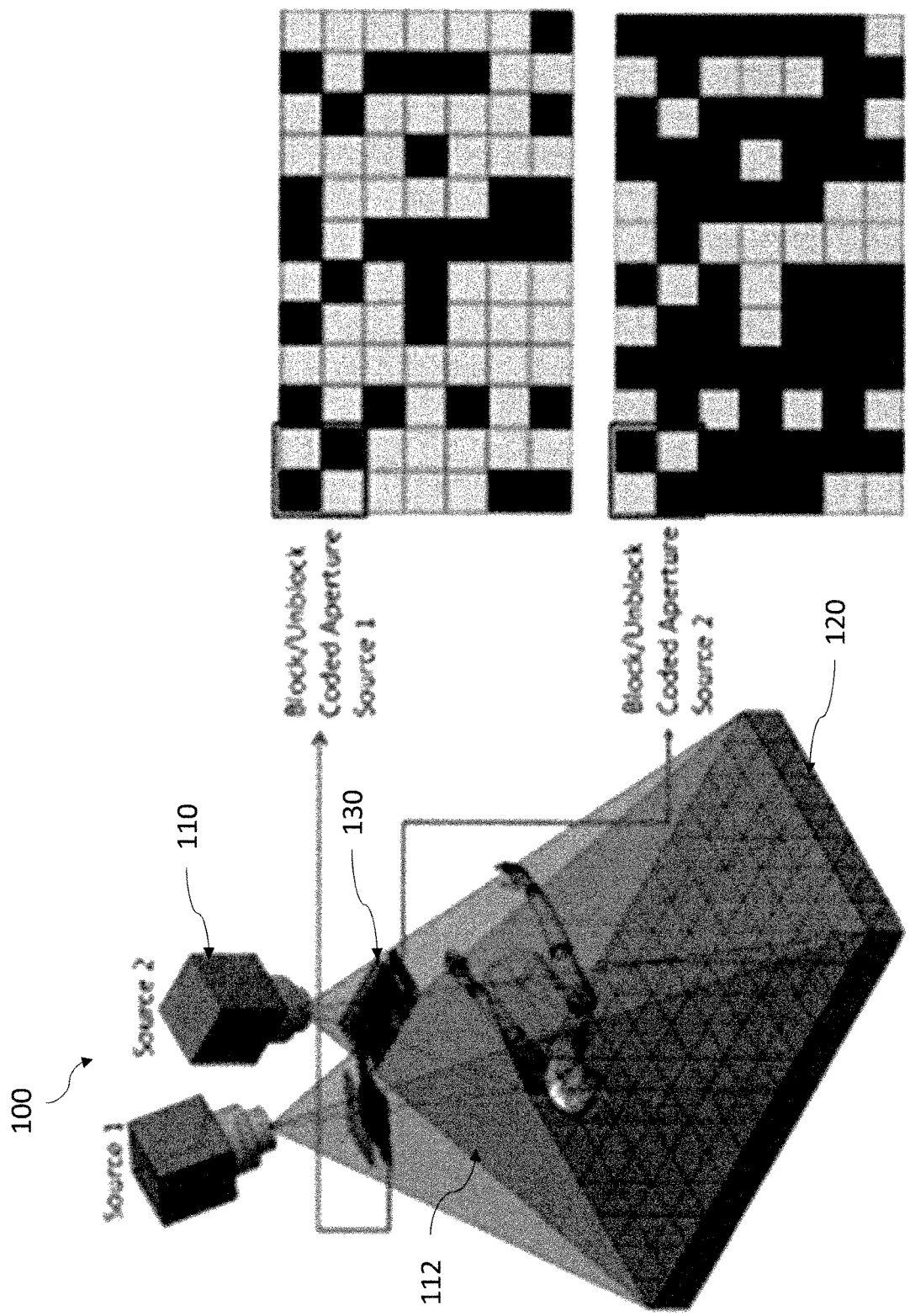
FIG. 6 is a schematic depicting additional non-limiting, exemplary steps for obtaining spectral CT images according to aspects of the invention.

FIG. 6 is a schematic depicting additional non-limiting, exemplary steps for obtaining spectral CT images. As illustrated by the embodiment shown in FIG. 6, spectral imaging systems 100 may include two or more X-ray generators 110 and a second structure 140 comprising two separate K-edge filters that together form a balanced pair. Each of the K-edge filters may be associated with a corresponding X-ray generator 110 and a block/unblock coded second structure 136 may be positioned before or after each of the K-edge filter. These block/unblock coded second structure 136 are, preferably, configured to be complementary with each other. In other words, the coded aperture elements of block/unblock coded second structure 136 associated with a particular detector pixel are such that only one of them has an unblocking element, while the others correspond to a blocking element. For example, as illustrated in FIG. 6, if the coded aperture of Source 1 has an unblocking element (e.g., an opening or aperture) in a particular position, the coded aperture of the Source 2 has a blocking element in such position.

FIGS. 7-10E illustrate non-limiting embodiments of spectral CT imaging systems utilizing different combinations of X-ray beam generators, X-ray beam detectors, and pixelated K-edge aperture structures.

Figure 7:
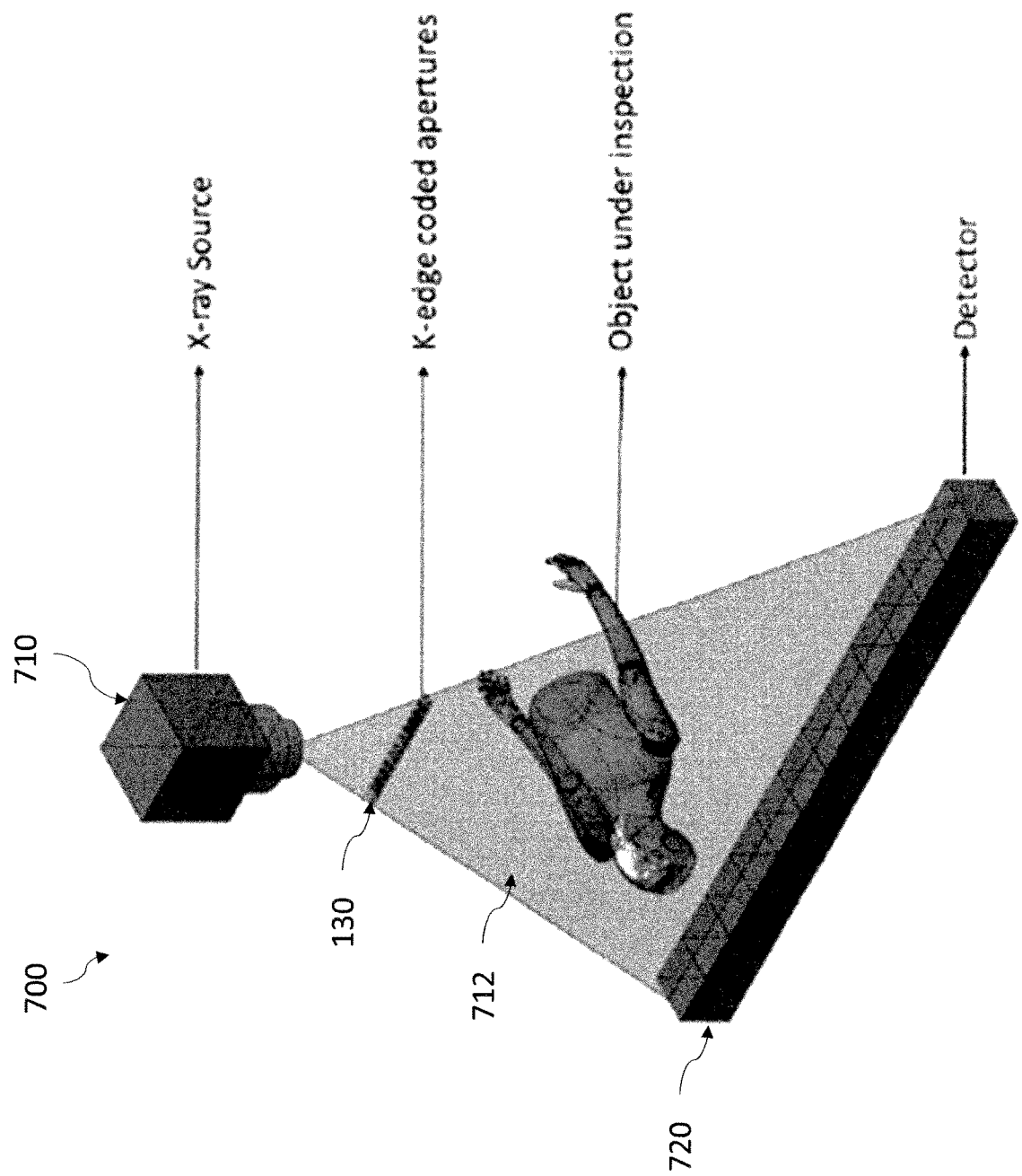
FIG. 7 depicts a spectral CT imaging system having an X-ray generator that produces fan beams and a X-ray line detector in accordance with aspects of the invention.

FIG. 7 illustrates a non-limiting embodiment of a spectral CT imaging system 700 that includes an X-ray beam generator 710 that produces X-ray fan beams 712 and an X-ray detector 720. X-ray beam generator 710 may be configured to include collimator or be configured such that plurality of generated X-ray beams 712 are fan beams, as shown in the FIG. 7. X-ray detector 720 is configured as a line detector in the illustrated embodiment. In this embodiment, to obtain a reconstruction of the two-dimensional slice being imaged, X-ray beam generator 710 and X-ray detector 720 rotate around the target to obtain projections at different angles. Pixelated K-edge aperture structure 130 may include different K-edge filters that are chosen from a set of balanced K-edge filters. In various embodiments, the selection of the set of balanced K-edge filters are random, uniform, or the same for all the positions but different for particular X-ray fan beams 712. Although pixelated K-edge aperture structure 130 is illustrated in FIG. 7 as being positioned between X-ray beam generator 710 and the target, pixelated K-edge aperture structure 130 may be positioned in front of or behind the target so long as pixelated K-edge aperture structure 130 is positioned between X-ray beam generator 710 and X-ray detector 720. Spectral CT imaging system 700 may also obtain projections by rotating the target while the position of X-ray generator 710 and X-ray detector 720 are stationary. The projections can be from limited angles in a limited range of the possible circular trajectory or they can be taken at multiple positions in the full 360° range.

Figure 8:
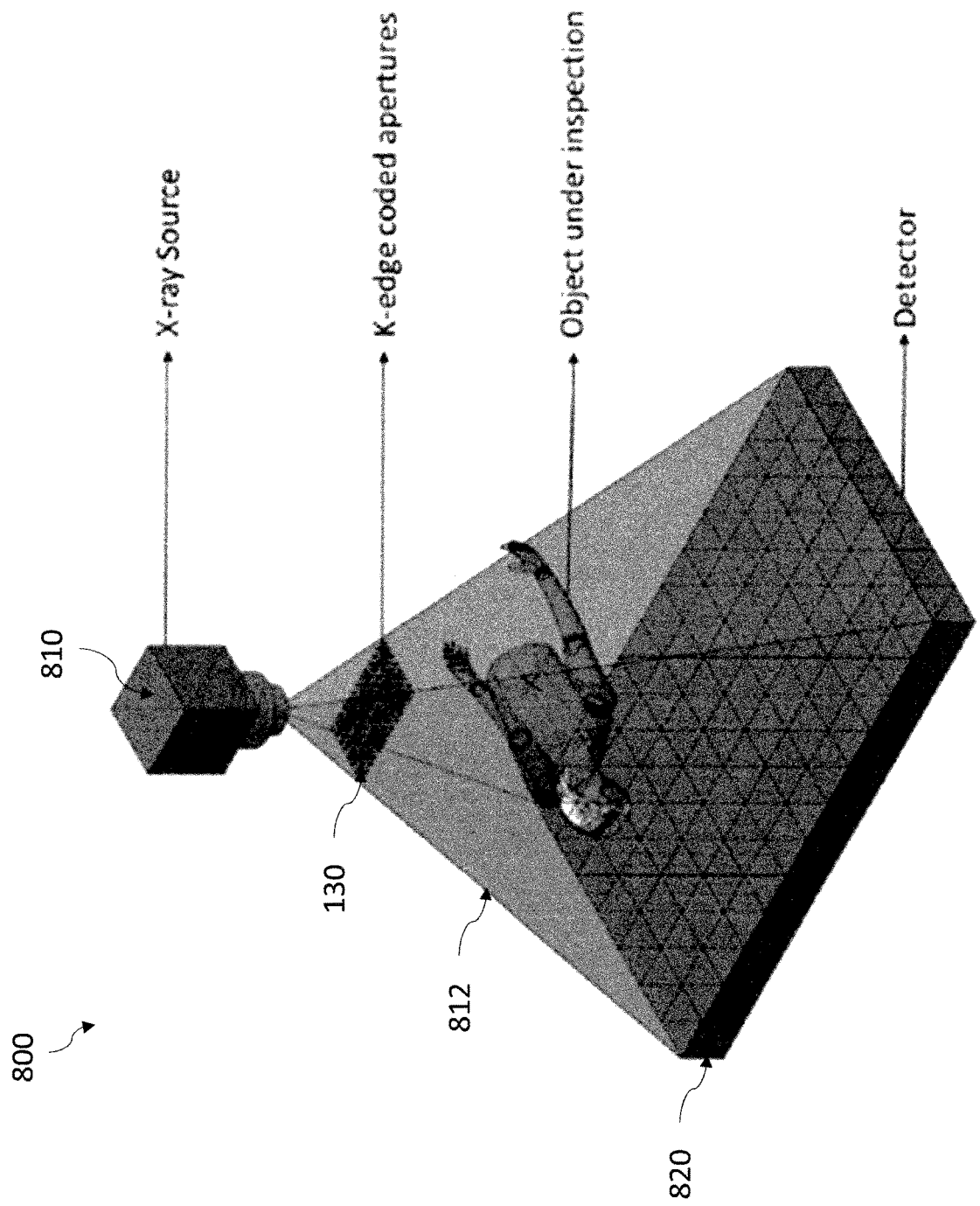
FIG. 8 depicts a non-limiting embodiment of a spectral CT imaging system having an X-ray generator that produces cone beams and a X-ray two dimensional detector according to aspects of the invention.

FIG. 8 illustrates a non-limiting embodiment of a spectral CT imaging system 800 that includes an X-ray beam generator 810 that produces X-ray cone beams 812 and an X-ray detector 820. X-ray generator 810 may be configured to have a collimator or be configured such that the X-ray illumination is a X-ray cone beam 812, while X-ray detector may be a two dimensional detector, as shown in FIG. 8. X-ray generator 810 and X-ray detector 820 may rotate around the target to obtain projections at different angles. Pixelated K-edge aperture structure 130 have different K-edge filters that are chosen from a set of balanced filters, as discussed herein. Although pixelated K-edge aperture structure 130 is illustrated in FIG. 8 as being positioned between X-ray beam generator 810 and the target, pixelated K-edge aperture structure 130 may be positioned in front of or behind the target so long as pixelated K-edge aperture structure 130 is positioned between X-ray beam generator 810 and X-ray detector 820. Spectral CT imaging system 800 may also obtain projections by rotating the target while the position of X-ray generator 810 and X-ray detector 820 are stationary. The projections can be from limited angles in a limited range of the possible circular trajectory or they can be taken at multiple positions in the full 360° range.

Figures 9A, 9B:
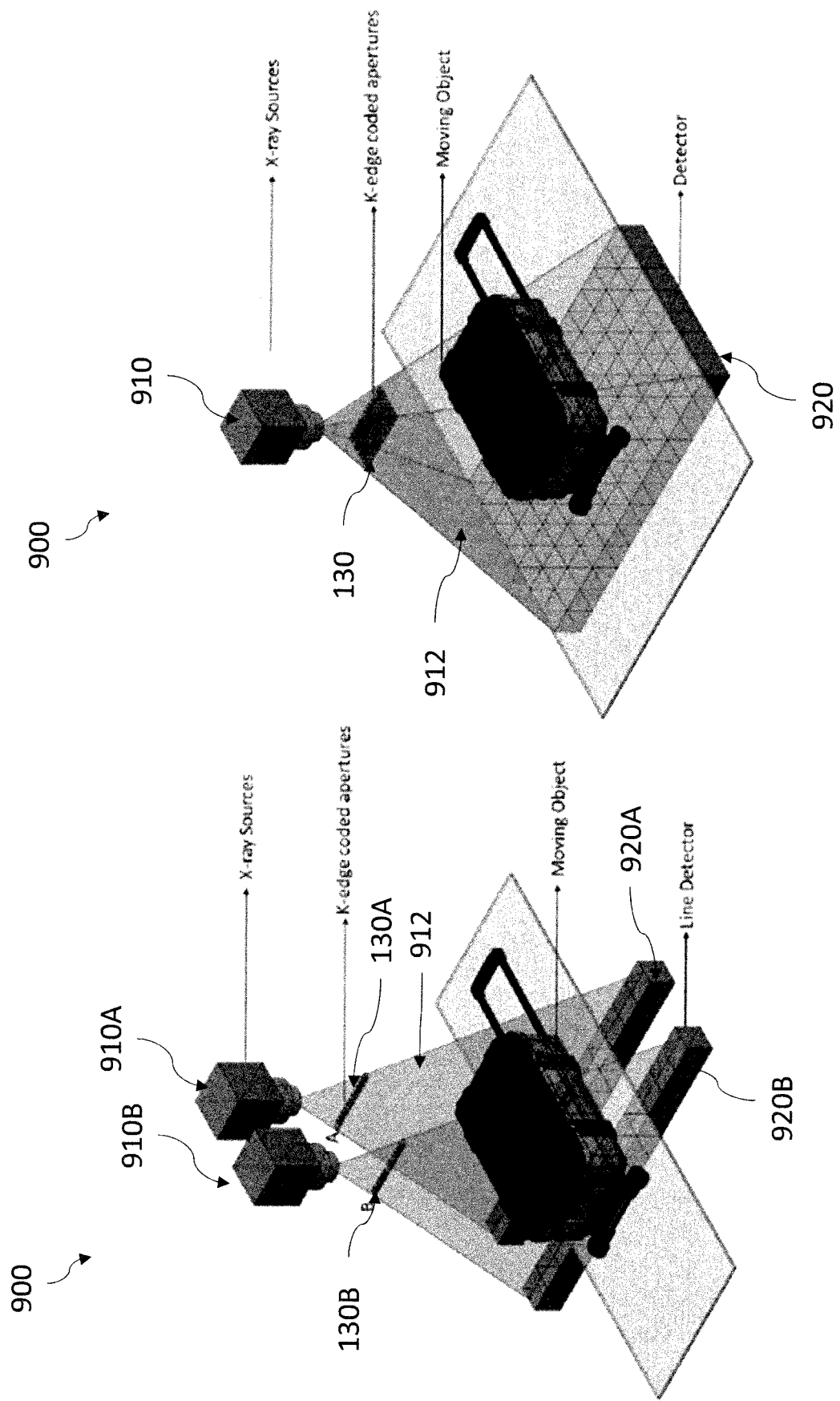
FIGS. 9A and 9B depict non-limiting embodiments of spectral CT imaging systems employing a conveyor belt in accordance with aspects of the invention.

FIGS. 9A and 9B illustrate non-limiting embodiments of a spectral CT imaging system 900 that includes an X-ray beam generator 910 that produces X-ray beams 912 and an X-ray detector 920. Spectral CT imaging system 900 as depicted in FIG. 9A includes a first X-ray generator 910A, a second X-ray generator 910B, a first pixelated K-edge aperture structure 130A, a second pixelated K-edge aperture structure 130B, a first X-ray detector 920A, and a second X-ray detector 920B. In one embodiment, the $n^{th}$ position for pixelated K-edge aperture structure 130A has the pair filter of the material contained in the $n^{th}$ position for pixelated K-edge aperture structure 130B, such that the measurements can be subtracted to obtain a monochromatic reading. Although X-ray detectors 920A and 920B are positioned horizontally with respect to the conveyer belt in FIG. 9A, in another embodiment X-ray detectors 920A and 920B may be positioned substantially parallel or at an angle with respect to the conveyer belt. Spectral CT imaging system 900, as depicted in FIG. 9B, includes an X-ray generator 910 that produces X-ray beams 912 in the form of X-ray cone beams and a two dimensional X-ray detector 920.

FIGS. 10A-10E illustrate non-limiting embodiments of a spectral CT imaging system 1000 that includes an X-ray beam generator 1010 that produces X-ray beams 1012 and an X-ray detector 1020. Spectral CT imaging system 1000 includes features that are employed similar to those discussed above with respect to spectral CT imaging systems 100 and 700-900, with details regarding those features omitted in order to avoid duplication.

Figure 10A:
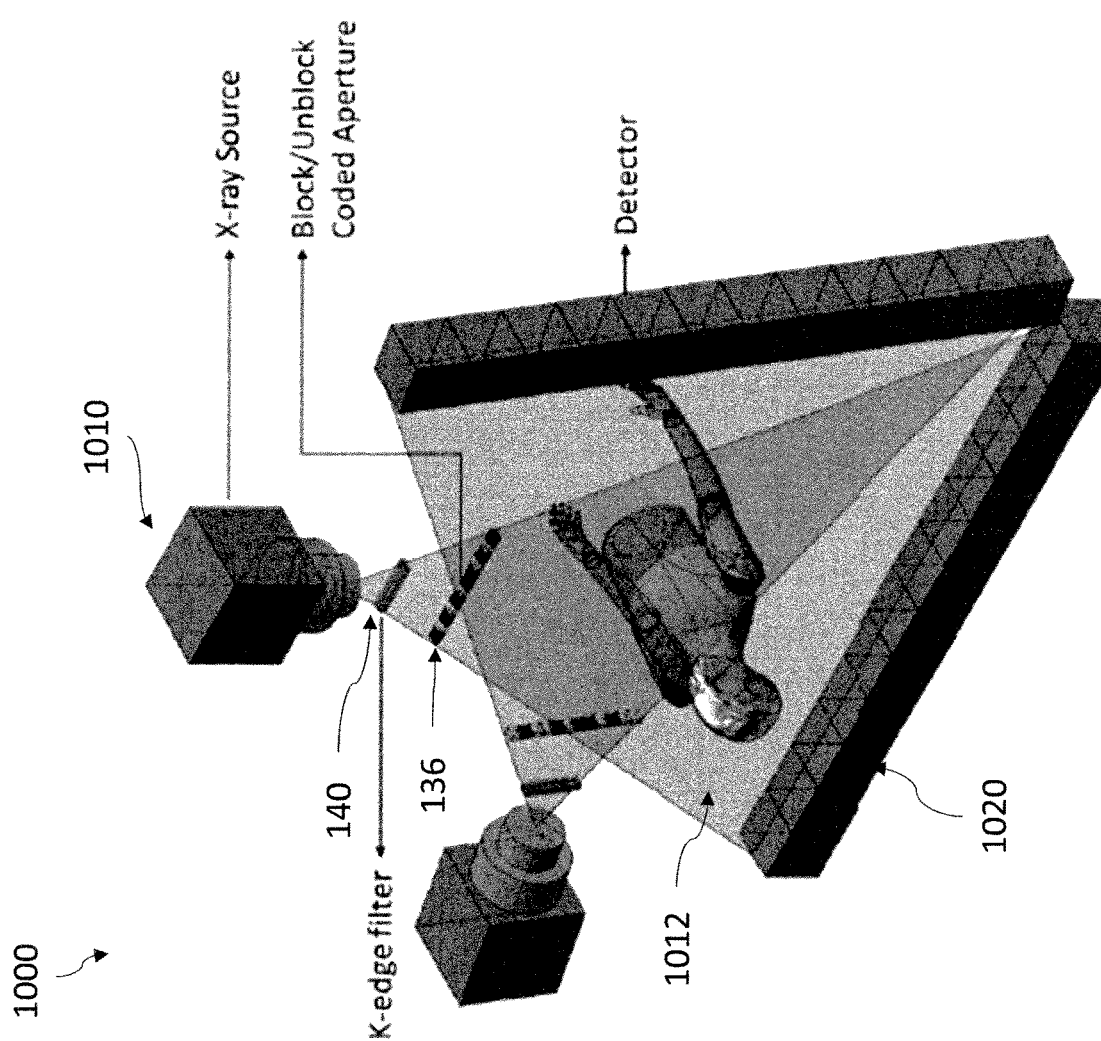
FIGS. 10A-10E depict non-limiting embodiments of spectral CT imaging systems according to aspects of the invention.
Figure 10B:
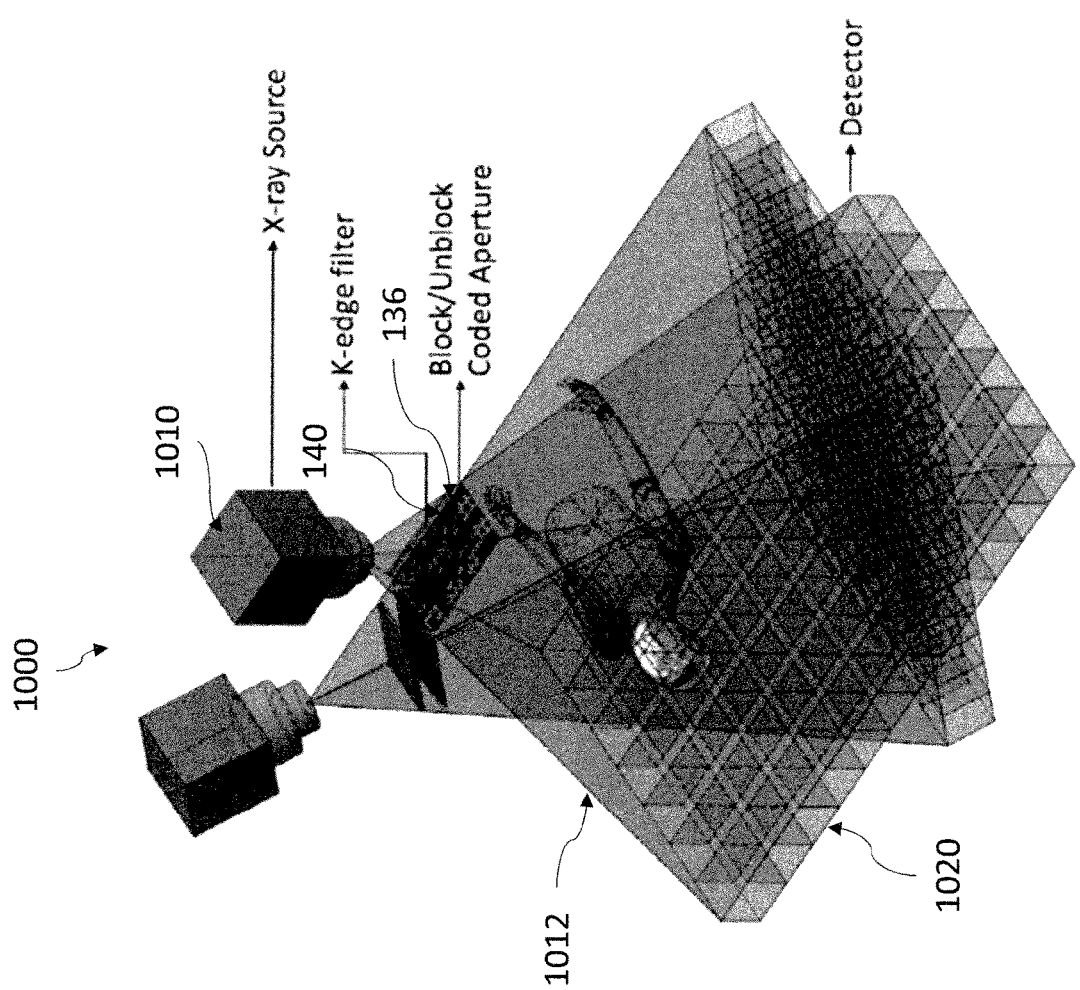
Figure 10C:
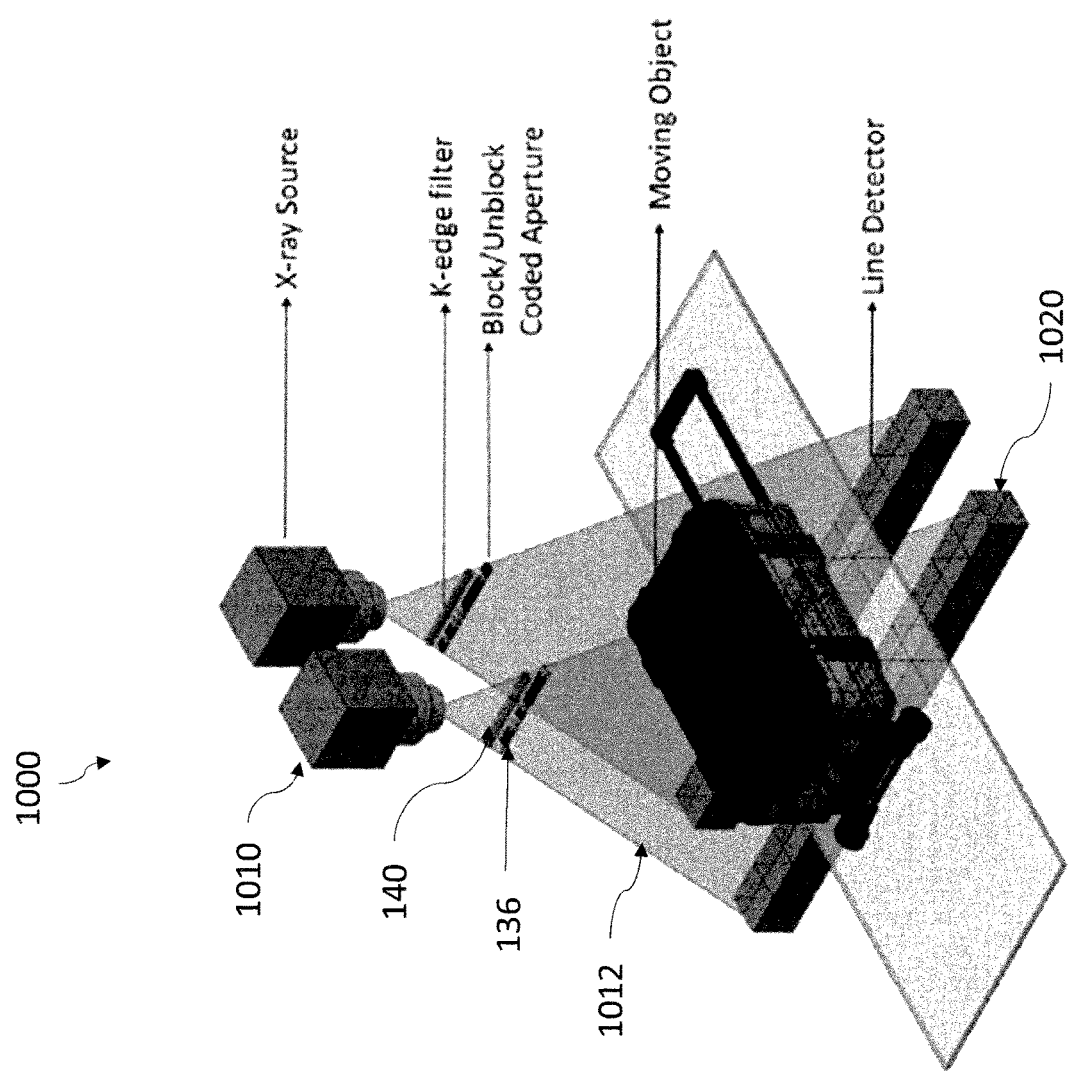
Figure 10D:
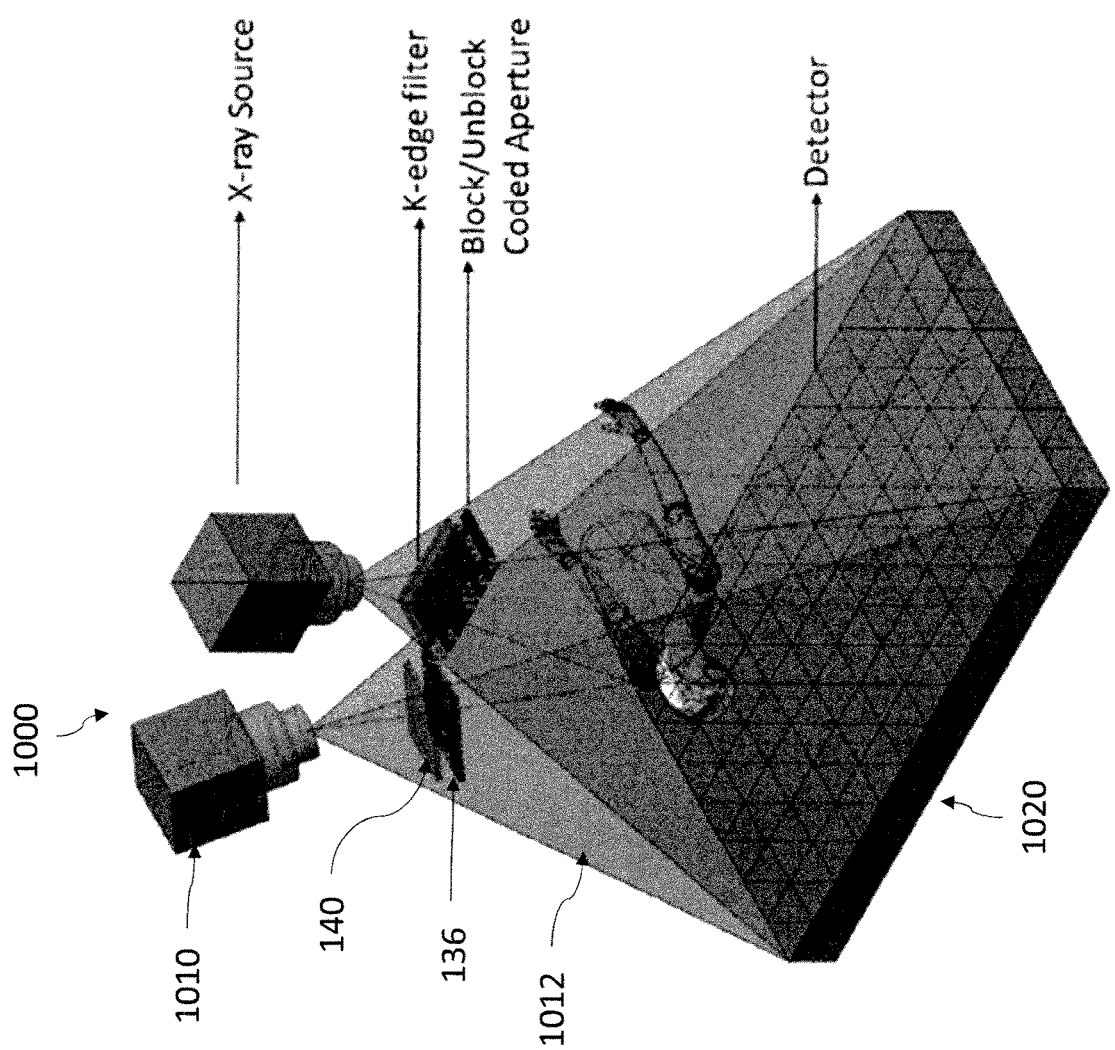
Figure 10E:
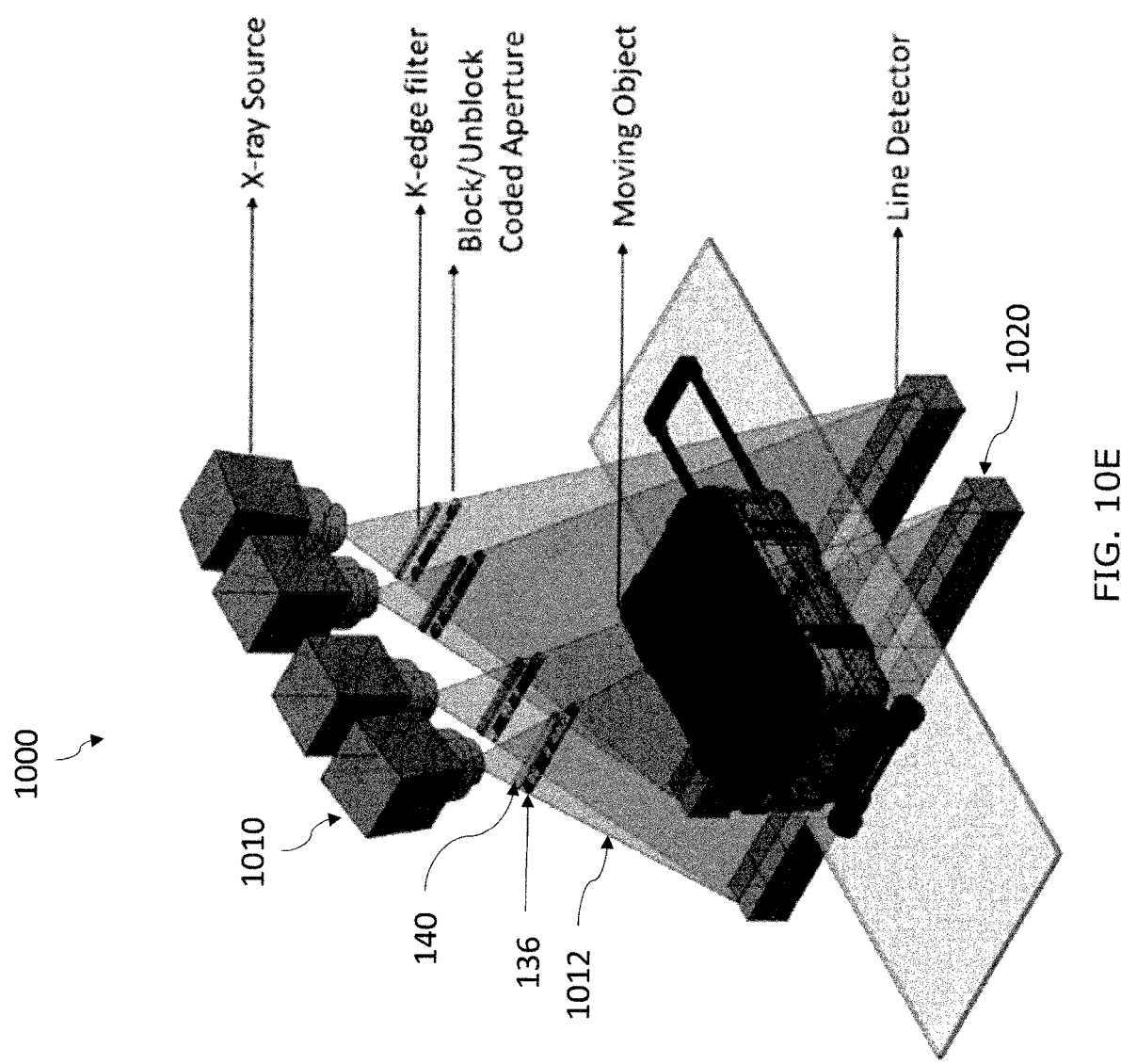

X-ray beam generator 1010 is illustrated in FIGS. 10-10E as producing a plurality of X-ray beams 1012 in the form of X-ray fan beams or X-ray cone beams, while X-ray beam detector 120 is illustrated as a line X-ray detector or a two dimensional X-ray detector. In FIGS. 10A-10E, pixelated K-edge coded aperture structure 130 is illustrated as including a first structure 136 (e.g., a block/unblock patterned structure) for pixelating the X-ray beams 1012 and a separate, second structure 140 comprising two separate K-edge filters for filtering X-ray beams 1012. A K-edge filter may be positioned between each of the X-ray generators 1010 and X-ray detector(s) 120. Under the circumstances where the target rotates and X-ray generator 1010 and X-ray detector 120 remain stationary, a different K-edge filter may be positioned in between of X-ray generator 1010 and X-ray detector 120 for each measurement taken. In an alternative embodiment, projections may be obtained by rotating the target while the position of X-ray generator 1010 and X-ray detector 1020 are stationary. The projections can be from limited angles in a limited range of the possible circular trajectory or they can be taken at multiple positions in the full 360° range. In embodiments of spectral CT imaging system 1000 having an X-ray generator 1010 that produces X-ray cone-beam, X-ray detector 102 and the target may be configured to remain stationary while X-ray generator 1010 rotates on an arch or moves in a linear trajectory over the target. In these embodiments, each projection is preferably paired with a different K-edge filter and a different first structure 136 having a plurality of opening 138 forming a different coded pattern for the X-ray beams 1012 transmitted therethrough. Additionally and/or alternatively, multiple X-ray generators 1010 may be available to obtain sequential projections at different positions (instead of rotating the same X-ray generators 101).

EXAMPLES

Non-limiting examples are described below to illustrate various implementations and simulated experiments of embodiments of the invention and/or to elucidate advantages associated with various embodiments of the invention.

Example 1

Simulated experiments were performed using conventional X-ray imaging systems with K-edge coded aperture masks to obtain spectrally multiplexed measurements used to reconstruct the energy-binned images. In this Example, filter pairs were aligned with each X-ray beam in a multi-shot architecture—therefore obtaining compressive measurements in both the spectral and spatial domains. This approach may be referred to herein as compressive spectral X-ray imaging or CSXI.

Quasi-monochromatic X-rays were be obtained using the balanced filter by subtracting the X-ray spectrum acquired with one filter from the spectrum acquired with the second filter of the pair. Specifically, the quasi-monochromatic curve was obtained at the energy bin between the K-edges of the filters. For the process used in this Example, two or more shots could be used in which the pixels of the coded apertures are chosen from a set of balanced Ross filters, such that a particular pair is assigned to a particular detector position.

The alternating direction method of multipliers (hereafter "ADMM") was used to solve the highly ill-posed problem by exploiting the inherent sparsity of X-ray images in the spatial domain and the low-rank structure of the data-cube. Although not completed in this Example, such processed image data may be further decomposed into basis functions to obtain material based images that are useful for diagnosis and analysis in medical and/or security applications.

For a polychromatic X-ray beam passing through an target, the X-ray attenuation at each energy level, E, was obtained from the polychromatic Beer-Lambert law as $$I(E)=S(E) \cdot Q(E) \cdot P(E) \exp(-\int_l \mu(l,E)dl) \quad \text{Equation 1}$$

where $\mu(l, E)$ is the linear attenuation coefficient of the target at the position l; $S(E)$ is the X-ray source spectrum; $Q(E)$ is the energy-dependent detector response; and $P(E)$ is the photon energy at the energy E. For photon counting detectors $P(E)=1$ and for conventional integrating detectors $P(E)=E$. That is, photon counting detectors reflect the number of photon counts in each energy bin. Integrating detectors, on the other hand, accumulate the intensity over the entire X-ray energy spectrum; thus, the contribution of each photon to the reading is weighted by its original energy. Let $I_0(E)=S(E) \cdot Q(E) \cdot P(E)$ be the intensity measured at energy E without any target in front of the X-ray source; then, for a conventional X-ray imaging system, with integrating detectors, the intensity registered by the $j^{th}$ detector element is given by:

$$I_j = \int_E I_0(E) \exp(-\int_l \mu(l,E)dl) dE. \quad \text{Equation 2}$$

If P is the total number of X-ray source positions and M is the number of detector elements in the detector array, then $j=1, \ldots, MP$. The integrated grayscale data cannot be used to reconstruct directly the energy-binned images $\mu(l, E)$, as it does not provide spectrally resolved data. To obtain quasi-monochromatic X-ray spectra Ross filter pairs were used. Ross filters consist of materials with nearly adjacent atomic numbers whose thicknesses are carefully matched such that the transmitted spectra are identical for all photon energies except in the narrow energy bin between their respective K-edges. The quasi-monochromatic measurements were then obtained by subtracting the X-ray intensity acquired using the filter with the lower K-edge from that with the higher K-edge in the Ross pair. Therefore, the bandwidth of the energy bin is defined by the difference between the K-edge energies of the two elements constituting the Ross pair.

Figure 11:
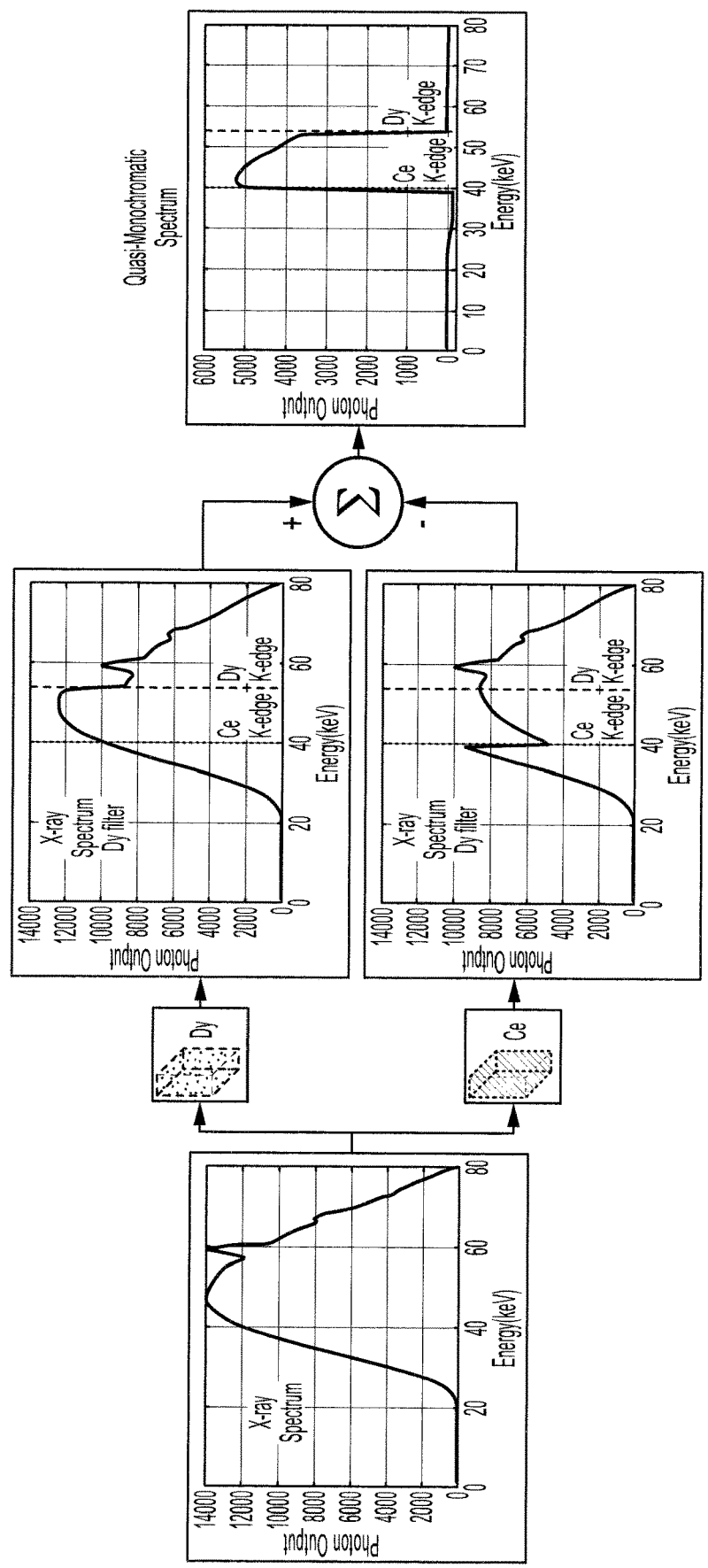
FIG. 11 is a schematic depicting a process to obtain a quasi-monochromatic X-ray spectrum using a Ross pair formed from dysprosium and cerium according to aspects of the invention.

FIG. 11 illustrates the process to obtain a quasi-monochromatic X-ray spectrum using the Ross pair constituted by Dysprosium (Dy) and Cerium (Ce). The thickness of each filter was set such that the X-ray transmission curves of the filtered spectra were nearly the same for both filters over the entire energy spectrum except within the narrow band between the K-edges of the elements. As shown in FIG. 11, by subtracting the spectrum filtered by Ce from the spectrum filtered by Dy a quasi-monochromatic spectrum between 40.4 keV and 53.8 keV was obtained.

To calculate the intensity of the X-ray beam at the energy E after passing through a homogeneous filter, the following equation was used.

$$I_f(E) = I_0(E) \exp[-\mu_f(E) \delta_{j,f}], \quad \text{Equation 3}$$

where $\mu_f(E)$ is the linear attenuation coefficient of the filter f at the energy E, and $\delta_{j,f}$ is the length of the intersection of the $j^{th}$ X-ray beam with the filter f. The latter is given by $\delta_{j,f} = \rho_f/\cos(\psi_j)$, where $\rho_f$ is the thickness of the filter and is the angle between the normal of the filter and the $j^{th}$ X-ray beam. Thus, the filtered measurements on the $j^{th}$ element using an integrating detector are given by:

$$I_j^f = \int_E I_f(E) \exp[-\int_l \mu(l,E)dl] dE \quad \text{Equation 4}$$

CSXI process here in this Example included only two scans to obtain the linear attenuation coefficient at all the energy bins; therefore, the scanning time and the radiation dose were reduced without compromising the image quality which is of paramount importance in medical imaging. CSXI process also used K-edge coded apertures as multiple material filters to obtain spatially and spectrally coded illumination projections of the target. For simplicity, in the simulated experiments of this Example, the coded apertures were assumed to have the same number of elements as the detector array and the coded aperture pitch was fixed to obtain one to one correspondence with the detector elements. More general scenarios where there is no one to one correspondence with the detector array would have the same forward model; however, computational methods to treat the pixel mismatch would have to be implemented such as the approach used for coded aperture snapshot spectral imaging (CASSI) systems.

Figure 12:
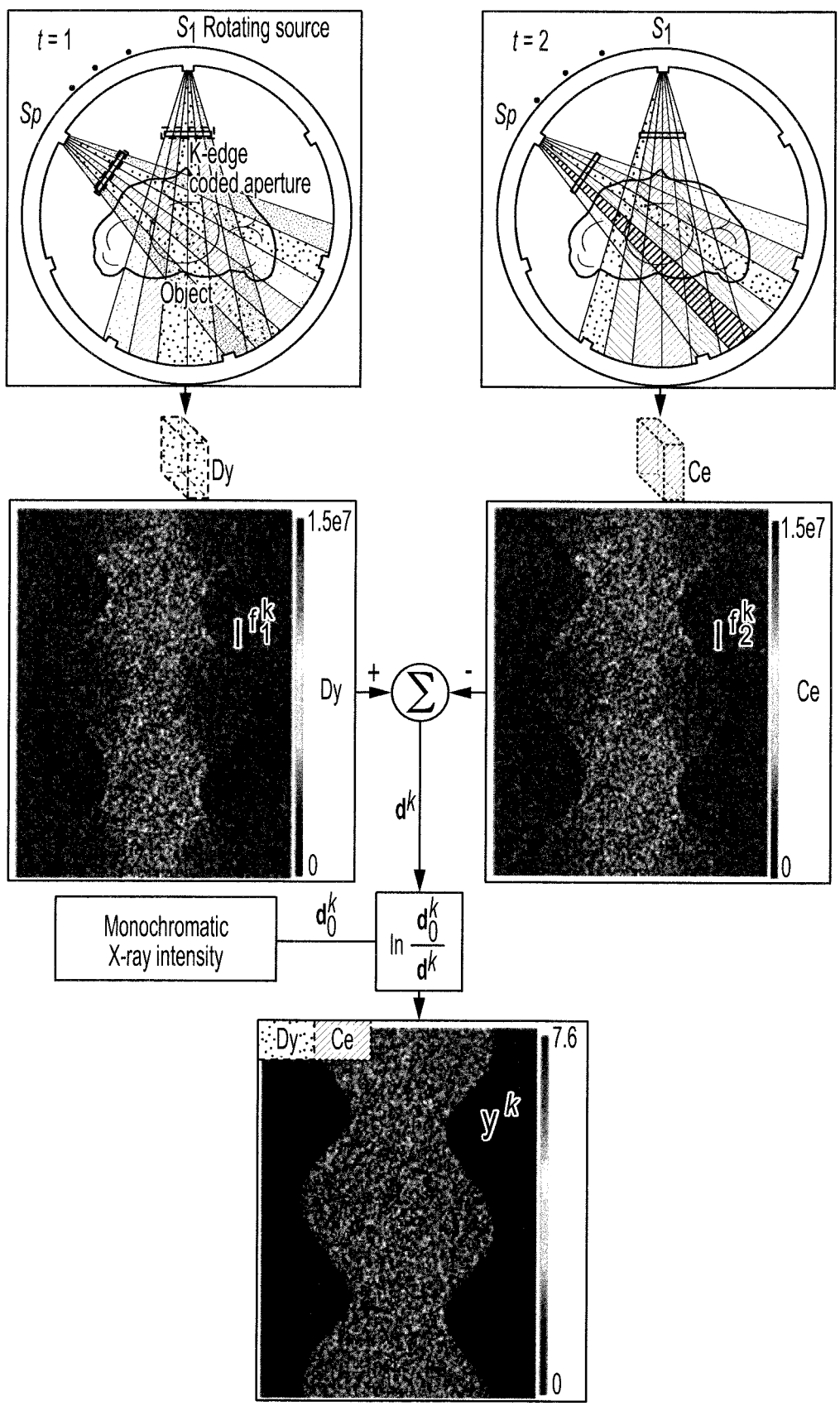
FIG. 12 is a schematic of a method for using a compressive spectral X-ray imaging (CSXI) system for a fan beam architecture, where two X-ray beam shots are projected through different materials in accordance with aspects of the invention.

Different coded aperture patterns were used for each view angle position $s_p$, where p=1, ..., P, and each shot t where t=1, ..., T as shown in FIG. 12, which depicts the CSXI system for a fan beam architecture with T=2 shots. It should be noted that the measurements obtained by a single scan were not sufficient for reconstruction since the quasi-monochromatic intensity was obtained by subtracting the X-ray intensities of a Ross filter pair. Thus, at least 2 scans were performed in which a Ross pair was assigned to each detector position j. In this way, in the first shot t=1, the K-edge coded aperture contained one of the materials of the pair in the position j and in the second shot, t=2, the coded aperture contained the other material from the pair in the same position, as shown in FIG. 12. Using these measurements, the quasi-monochromatic measurement for the $k^{th}$ energy bin at the $j^{th}$ detector element could be obtained as:

$$d_j^k = I_j^{f1^k} - I_j^{f2^k} \qquad \text{Equation 5}$$

where $I_j^{f1^k}$ and $I_j^{f2^k}$ are the measurement taken by the filters with higher and lower k-edges in the Ross pair associated with the $k^{th}$ energy bin, respectively. FIG. 2 depicts the measurements obtained using Dy and Ce, $I^{f1^k} = [I_1^{f1^k}, \ldots, $ where $I_{MP}^{f1^k}]^T$ and, $I^{f2^k} = [I_1^{f2^k}, \ldots, $ where $I_{MP}^{f2^k}]^T$ respectively. The discretized set of measurements, referred to as the sinogram, corresponds in each case to the measurements of the detectors paired with the respective filter. Note both sinograms contain information in the same location such that the filtered measurements can be subtracted to obtain the quasi-monochromatic sinogram. The measurements obtained from Equation 5 can be considered mono-energetic, and thus they can be described by the Beer-Lambert Law as $$d_j^k = d_{j0}^k \exp\left[-\int_\ell \mu(\ell, k) d\ell\right],$$

where $d_{j0}^K$ is the quasi-monochromatic intensity obtained using the Ross filter pair when there is no target in front of the X-ray source, and μ (l, k) is the linear attenuation coefficient at the $k^{th}$ energy bin. Consequently, the log-transformed measurements at the $k^{th}$ energy bin can be obtained as:

$$y_j^k = \ln\frac{d_{j0}^k}{d_j^k} \qquad \text{Equation 6}$$

Equation 6 only applies to the kth energy bin corresponding to the Ross filter pair assigned to the position j, for any other energy bins $y_j^m = 0$, whenever m does not equal k. For example, the Ross pair Dy-Ce corresponds to the second energy bin, k=2, then for all j positions where Dy-Ce is assigned $$y_j^k = \ln\frac{d_{j0}^k}{d_j^k}$$

for K=2, and $y_j^k = 0$, where k does not equal 2. As a result, the energy-binned sinograms are sparsely distributed as shown in FIG. 12. Five different filter materials [Molybdenum (Mo), Cerium (Ce), Dysprosium (Dy), Erbium (Er) and Tungsten (W)] were used for the K-edge coded apertures. The Ross pairs, their thicknesses (ρ) and the corresponding energy bins for these materials are shown in Table 1, provided on the following page. Discretizing the line integrals and the linear attenuation coefficient μ(l, k), the energy-binned measurements $y^k = [y_1^k, y_1^k, \ldots y_{MP}^k]^T$ are given by the following linear model:

$$y^k = C^k H x^k \qquad \text{Equation 7}$$

where $x^k \in R^{N^2 \times 1}$ is the vectorized linear attenuation coefficient μ(l, k) of the N×N discretized target under $H \in R^{MP \times N^2}$ is the CT system matrix such that the weights $H_{j,i}$ account for the hardware settings, that is, $H_{j,i}$ corresponds to the intersection of the $j^{th}$ ray with the $i^{th}$ pixel in the target, and $C^k$ is the coded aperture matrix. Each row of the matrix, H, corresponds to a particular detector element j, and each detector is associated with a particular Ross filter pair which in turn is associated with a particular energy bin k. Thus, the elements of the coded aperture matrix $C^k$ select the rows of the matrix H associated with the Ross filter pair that corresponds to the kth energy bin. Mathematically, the coded aperture matrix $C^k$ is defined as a diagonal binary matrix, where $[C^k]_{j,j} = 0$ for 3 does not equal 1 and $[C^k]_{j,j} = 1$ if the K-edge coded aperture element associated with the $j^{th}$ detector contains the elements of the Ross filter pair corresponding to the $k^{th}$ energy bin, otherwise $[C^k]_{j,j} = 0$.

TABLE 1

| k | Filter 1 | Filter 2 | Energy (keV) | $\rho_1$ (μm) | $\rho_2$ (μm) |
|---|----------|----------|--------------|---------------|---------------|
| 1 | Ce | Mo | 20.0-40.4 | 52.8 | 74.7 |
| 2 | Dy | Ce | 40.4-53.8 | 30.6 | 52.8 |
| 3 | Er | Dy | 53.8-57.5 | 26.7 | 30.6 |
| 4 | W | Er | 57.5-69.5 | 9.9 | 26.7 |

Figure 13:
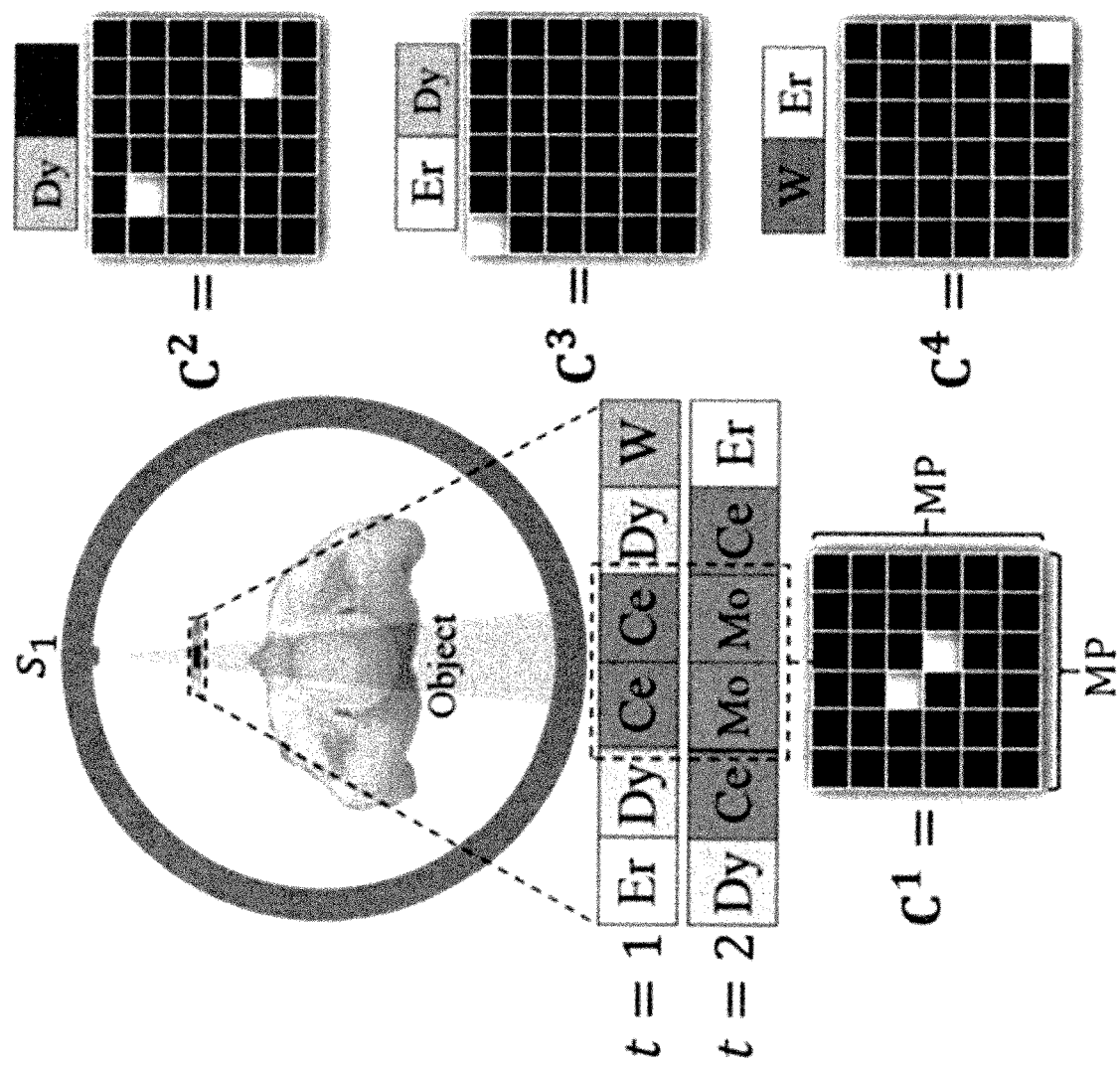
FIG. 13 is a schematic illustrating the coded aperture matrices for a system according to aspects of the invention.

FIG. 13 shows the coded aperture matrices for a system with M=6, P=1, T=2, and the filter pairs in Table 1. The first energy bin was defined by the pair Ce-Mo, for the example in FIG. 13, this filter pair was assigned to j=3 and j=4, thus the only non-zero elements in the coded aperture matrix were $[C^1]_{3,3} = [C^1]_{4,4} = 1$. The coded apertures for the remaining pairs were also depicted for the source position $s_1$.

The implementation of coded aperture masks with a pixel pitch having a one to one correspondence with the pixels on the detector can be a challenge due to the magnification factor when the codes are placed close to the source and before the target under inspection. A generalized model when a coded aperture element impinges onto multiple detector elements could be developed. Another approach is to model the system in which the coded aperture mask is located after the target and close to the detector. If the coded aperture elements have a one to one correspondence with the pixels on the detector, the measurements from an integrating detector when the mask is placed on the detector side are given by:

$$I_j^f = \int_E I_0(E)\exp\left\{-\left[\int_\ell \mu(\ell, E)d\ell + \mu_f(E)\delta_{j,f}\right]\right\}dE \qquad \text{Equation 8}$$

$$= \int_E I_0(E)\exp[-\mu_f(E)\delta_{j,f}]\exp\left[-\int_\ell \mu(\ell, E)d\ell\right]dE$$

where $\mu_f(E)$ is the linear attenuation coefficient of the filter f at the energy E, and, $\delta_{j,f}$ is the length of the intersection of the $j^{th}$ X-ray beam with the filter. Note, equation 8 is equivalent to the result obtained in Equation 4. Thus, the formulation is also valid when the coded aperture is placed on the detector side.

Ross filter pairs were assigned randomly to each detector element j following a uniform distribution; as a result, the number of measurements per energy bin is given by D=MP/K, where K is the total number of energy bins. The reconstruction of each energy bin is thus a highly ill-posed problem. Hence, to effectively recover the data cube from the compressed measurements, regularization constraints were added based on the structure of the data. In this Example, a joint sparse and low-rank optimization method was used. This approach seeks to jointly minimize the $l_1$ norm of the sparse representation of the data cube, and its nuclear norm. Furthermore, the tensor modeling was used to formulate the reconstruction problem. The following concepts are used in the remaining of the paper:

A. Tensor Modeling

1) Vectorization: Denoted by $\text{vec}(\chi)$, where vec: $R^{Q1 \times Q2 \times \ldots \times QN} \to R^{Q1 \cdot Q2 \cdots QN}$ is an operator that stacks the entries of a tensor in reverse lexicographical order into a $Q_1 Q_2 \ldots Q_N$-long column vector [24].

2) Unfolding: For a tensor $\chi$, the matrix unfolding denoted by $\chi_{(n)}$=Unfold n-th $(\chi)$ is defined by the mapping of: $R^{Q1 \times Q2 \times \ldots \times QN} \to R^{Qn \times (Qn+1 \cdot Qn+2 \ldots QN \cdot Q1 \cdot Q2 \ldots Qn-1)}$. The resulting matrix $\chi_{(n)}$ is a 2D matrix with $Q_n$ rows and $Q_{n+1} \cdot Q_{n+2} \ldots Q_N \cdot Q_1 \cdot Q_2 \ldots Q_{n-1}$ columns.

3) Folding: It is the inverse operator of unfolding and it is defined by $\chi$=Fold n-th$(\chi_{(n)})$ [8].

Using these concepts, the fan beam model used in this Example can be generalized to multiple geometries by representing the spectral linear attenuation coefficients with a tensor $X \in R^{Q1 \times Q2 \times \ldots \times Q\xi+1}$, where $\xi$ is the dimensionality of a single energy X-ray image. For instance, $\xi$=2 for fan-beam and parallel beam CT, $\xi$=3 for cone-beam CT and $\xi$=4 for dynamic cone beam CT. Without loss of generality, the remaining of this Example treats the inverse problem for a fan-beam system; therefore, the tensor X is a multi-dimensional matrix $\in R^{N \times N \times K}$, where the first two dimensions are spatial, the third is the energy dimension, and $\text{vec}(X) = [x^{1\,T}|x^{2\,T}|\ldots|x^{K\,T}]^T$. The spectral CT model in (7) can thus be generalized as:

$$y = A(x) = \left[[A^1 x^1]^T|\ldots|[A^k x^k]^T\right]^T$$

where y is the vertical concatenation of the quasi-monochromatic sinograms $y^k$ $A^k$=$C^k$H is the sensing matrix for the $k^{th}$ energy bin and A (*) is the tensor expression used to generalize the forward projection above. As it can be seen, the reconstruction of X from the measurements y describes an ill-posed problem that cannot be solved using traditional LS approaches. Nonetheless, the compressive sensing principles can be used to recover the data-cube without loss of reconstruction fidelity. This framework can be used as long as vec(X) is sufficiently sparse in some basis $\psi$ and such basis is incoherent with the forward measurement matrix. Let X be represented by $\text{vec}(X)=\psi[\text{vec}(\theta)]$, where $\theta$ is the sparse tensor representation of the object, and $\psi \in R^{N^2 K \times N^2 K}$ is the representation basis. Then, the sparse representation of the object x can be reconstructed by solving the following optimization problem:

$$\hat{\theta} = \text{argmin } \tfrac{1}{2}\|y - A(X)\|_2^2 + \lambda_1 \|\text{vec}(\hat{\theta})\|_1$$

B. CSXI Reconstruction via ADMM

An additional regularization constraint is added to the inverse problem, above, to take into account the correlation across spectral channels. This is achieved by introducing a low-rank constraint on $\chi$, such that:

$$\hat{\theta} = \text{argmin } \tfrac{1}{2}\|y - A(X)\|_2^2 + \eta_1\|\text{vec}(\hat{\theta})\|_1 + \eta_*\|\chi\|_*.$$

The ADMM algorithm is adapted to solve immediately preceding equation as it provides the necessary tools to split the optimization problem into small convex optimization problems that can be solved using simpler algorithms. When the augmented Lagrangian is calculated, two intermediate variables to separate the $l_1$, $l_2$ and nuclear norm components are introduced. Thus, immediately preceding equation is transformed as follows:

$$(X, D, B) = \underset{X,D,B}{\text{argmin}} \tfrac{1}{2}\|y - A(X)\|_2^2 +$$

$$\lambda*\|D\|_* + \lambda_1\|B\|_1 + \mu*\|D - X - V\|_2^2 + \mu_1\|B - \Psi^{-1}(X) - W\|_2^2$$

The problem is then split into three different sub-problems summarized in Algorithm 1. Step 2 of the algorithm is an $l_2$ minimization problem which was solved using the conjugate gradient (CG) algorithm with a fixed step size, and the solution for Step 3 and Step 4 can be found as:

$$D^{\tau+1} = \frac{1}{\xi+1}\sum_{\eta=1}^{\xi+1} \text{fold}(S_\xi\{X_{(n)}^{\tau+1} + V_{(n)}^\tau\}),$$

$$B^{\tau+1} = \text{softshrink}\{\Psi^{-1}(X^{\tau+1}) + W^\tau, \lambda_1/\mu_1\},$$

respectively; where $\in = \lambda^*/\mu^*$, $S_\in\{\bullet\}$ is the shrinkage operator with parameter $\in$, and $\tau$ is the iteration number. Note $X_{(n)}$ and $V_{(n)}$ are the matrices obtained by applying the unfolding operator to the tensors $\chi$ and V, respectively.

---

Algorithm 1 ADMM for CSXI reconstruction

---

Input: $D_0 = X_0$, $B_0 = \psi^{-1}(X_0)$ and $V_0 = W_0 = 0$.

1: for $\tau = 0$ to $\max_{iter} - 1$ do

2:
$$\mathcal{X}^{\tau+1} = \underset{\mathcal{X}}{\text{argmin}} \tfrac{1}{2}\|y - \mathcal{A}(\mathcal{X}^\tau)\|_2^2 + \mu_*\|\mathcal{D}^\tau - \mathcal{X}^\tau - \mathcal{V}^\tau\|_2^2 + \mu_1\|\mathcal{B}^\tau -$$
$$\Psi^{-1}(\mathcal{X}^\tau) - \mathcal{W}^\tau\|_2^2$$

3:
$$\mathcal{D}^{\tau+1} = \underset{\mathcal{D}}{\text{argmin}} \lambda_*\|\mathcal{D}^\tau\|_* + \mu_*\|\mathcal{D}^\tau + \mathcal{X}^{\tau+1} - \mathcal{V}^\tau\|_2^2$$

4:
$$\mathcal{B}^{\tau+1} = \underset{\mathcal{B}}{\text{argmin}} \lambda_1\|\mathcal{B}^\tau\|_1 + \mu_1\|\mathcal{B}^\tau - \Psi^{-1}(\mathcal{X}^{\tau+1}) - \mathcal{W}^\tau\|_2^2$$

-continued

Algorithm 1 ADMM for CSXI reconstruction

5: $\mathcal{V}^{\tau+1} = \mathcal{V}^\tau + \chi^{\tau+1} - \mathcal{D}^{\tau+1}, \mathcal{W}^{\tau+1} = \mathcal{W}^\tau + \Psi^{-1}(\chi^{\tau+1}) - \mathcal{B}^{\tau+1}$
6: end for
7: return $\chi^{\tau+1}$ C. Initialization The X-ray attenuation coefficients vary smoothly and have sharp boundaries. Total variation (TV) regularization is good reconstruction method for such cases, as it is robust to noise and the edges in the reconstructions are well-defined. Hence, in order to find a suitable initialization point for the ADMM algorithm, the energy-binned images $x^k$ are reconstructed from the corresponding quasi-monochromatic sinograms by solving the following minimization problem independently for each energy bin:

$$x^k = \underset{x^k}{\operatorname{argmin}} \; \|y^k - A^k X^k\|_2^2 + \lambda TV(x^k), x^k$$

where $\lambda$ is a regularization constant, $\|.\|_2$ corresponds to the 1 norm and TV(x) is the total variation of x defined as $\Sigma^2 \sqrt{(\Delta_i^h x)^2 + (\Delta_i^v x)^2}$ where $\Delta_i^h$ and $\Delta_i^v$ are the horizontal and vertical first-order local difference operators respectively. In this Example, the inverse problem described immediately above is solved independently for each energy bin using the two-step iterative shrinkage/thresholding algorithm (TwIST) and the result was used as the initial value for the ADMM algorithm detailed in Algorithm 1.

Example 2

Figure 14:
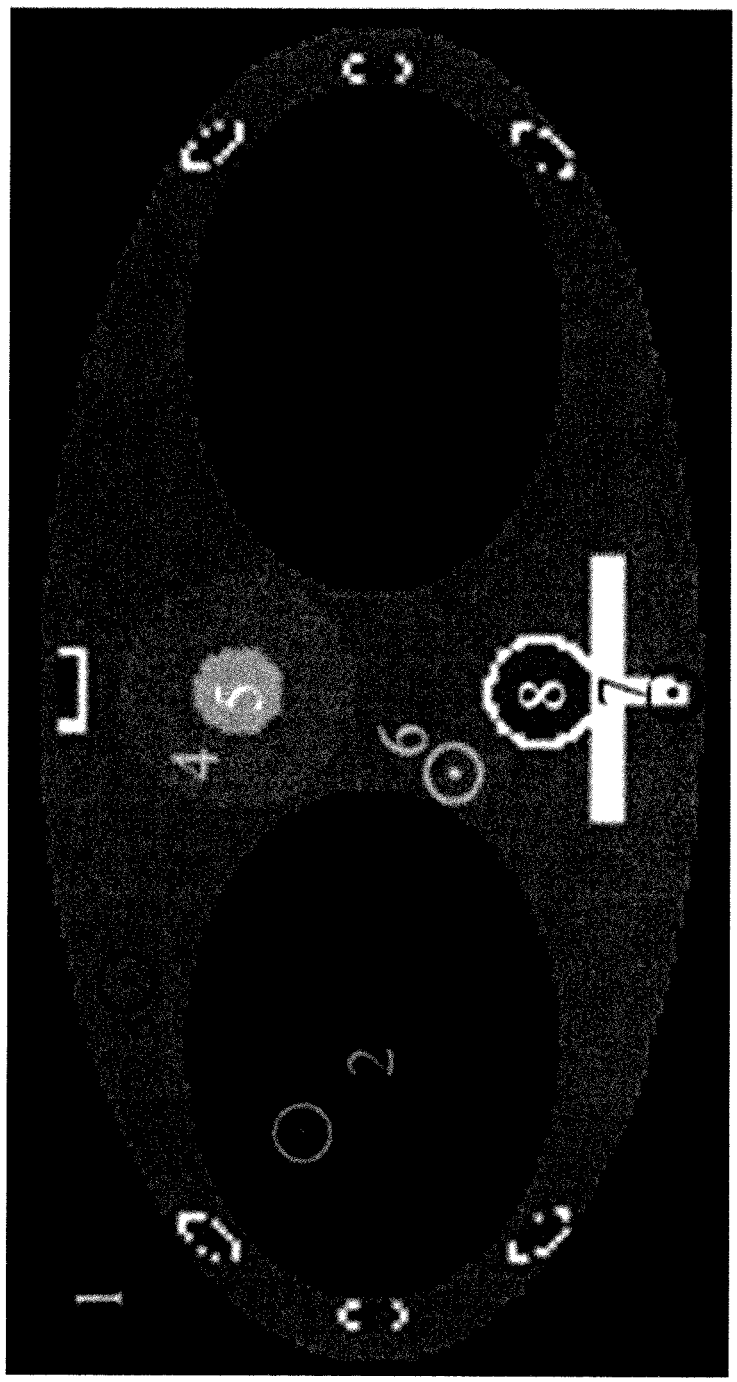
FIG. 14 illustrates a thorax phantom tested in accordance with aspects of the invention.

A simulated experiment for an X-ray fan beam system with K-edge coded apertures was performed using a 256×256 modified Forbild thorax phantom generated using the CONRAD software and the processes discussed in Example 1. The modified phantom consists of eight different materials to simulate lung, heart, artery, bone, soft tissue, air, iodine, and marrow. FIG. 14 shows the thorax phantom tested in this Example, with the tissues and materials defined in Table 2, provided below.

TABLE 2

| Number | Material | Density (g/cm³) |
| --- | --- | --- |
| 1 | Air | 0.00 |
| 2 | Lung | 0.26 |
| 3 | Average Soft Tissue | 1.00 |
| 4 | Heart (Blood) | 1.06 |
| 5 | ROI (0.9% Iodine + 99.1% Blood) | 1.09 |
| 6 | Artery (Blood) | 1.06 |
| 7 | Bone | 1.50 |
| 8 | Marrow | 0.98 |

The mass attenuation coefficient were obtained from the National Institute of Standards and Technology (NIST) X-ray attenuation databases. The X-ray filtered spectra $I_f(E)$ were simulated at 80 keV using the Spektr software and energy weighted integrals over 1 keV spectral steps were obtained for each filtered measurement according to Equation 4 from Example 1. The projection data were simulated using the ASTRA tomography toolbox for a regular fan-beam X-ray system architecture with P=450 view angles and M=336 detector elements per angle. The X-ray fan beam covered a 43.52 cm diameter field of view and the dimensions of the discretized target were 40 cm×40 cm. A copper (Cu) filter of 0.25 mm was placed in front of the X-ray source to filter the energies lower than 20 kV and the thicknesses of the elements of the Ross filter pairs were matched precisely to obtain energy-binned sinograms.

Figure 15:
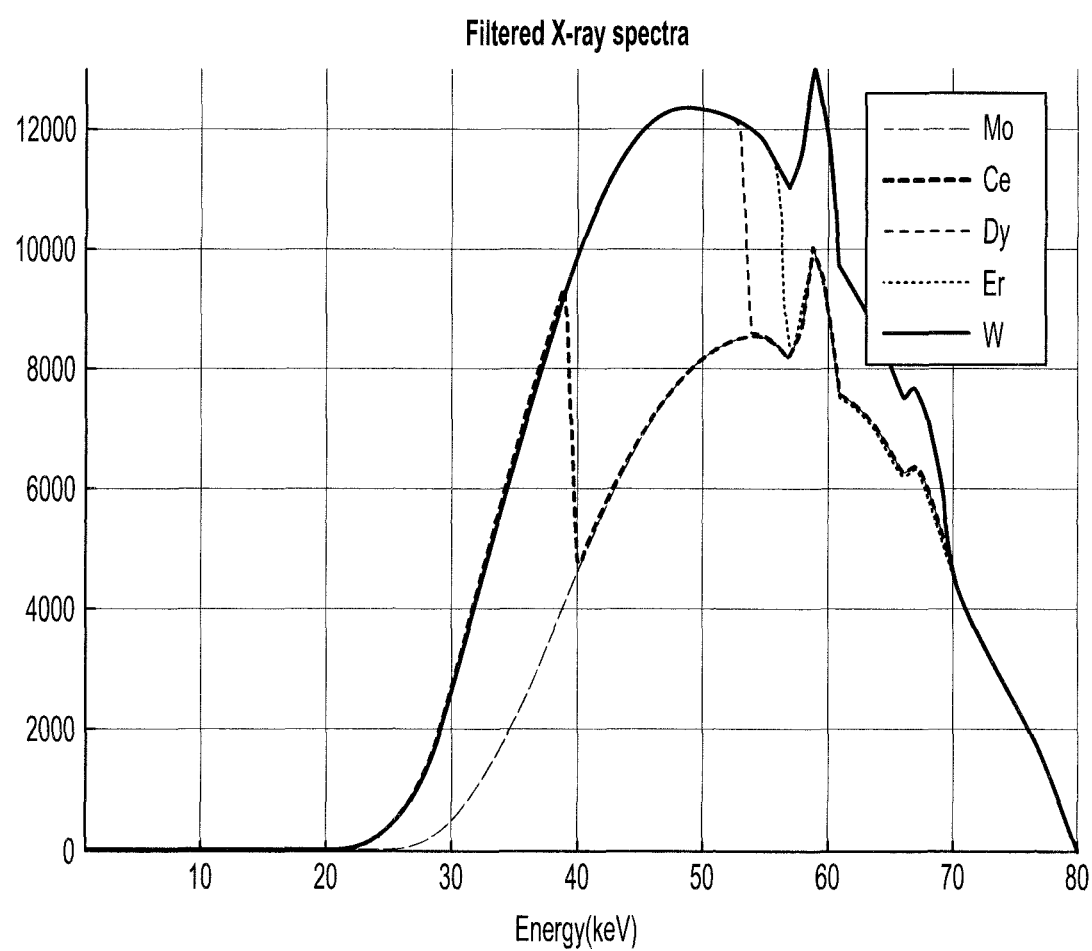
FIG. 15 is a graph of the energy spectra of the simulated 80 kV X-ray source after being transmitted through certain K-edge filters according to aspects of the invention.

After matching the Ross filter pairs, the thickness of the Mo, Ce, Dy, Er, and W filters were set to be 74.7, 52.8, 30.6, 26.7 and 9.9 µm respectively. The energy bins defined by these Ross filter pairs were 20.0-40.4, 40.4-53.8, 53.8-57.5, and 57.5-69.5 keV, for k=1, 2, 3, 4 respectively, as detailed in Table 1 from Example 1. The filter pairs assigned to each detector position j were chosen randomly from Ce-Mo [20.0-40.4], Dy-Ce [40.4-53.8], Er-Dy [40.4-53.8] and W-Er [57.5-69.5]. That is if Er-Dy was assigned to the detector position j=1, then in the first scan, the K-edge coded aperture contained Er at the position j=1 and in the second scan it contained Dy at the same position. FIG. 15 depicts the energy spectra of the simulated 80 kV X-ray source seen through the five different filters. Additionally, the resulting log-transformed measurements, $y^k$, were determined and the sinogram images were transformed using a gamma correction with γ=0.4 to improve the visualization contrast.

To evaluate the performance of the CSXI system and the reconstruction algorithm discussed in Example 1, comparative reconstructions were produced using the system disclosed in Y. Rakvongthai et al., "Spectral CT using multiple balanced K-edge filters," IEEE TRANS. ON MEDICAL IMAGING, vol. 34, no. 3, pp. 740-747, March 2015 (hereafter "Rakvongthai"), which incorporated herein for all purposes. The system proposed in Rakvongthai will be referred to as 5 Shot K-edge filtering (hereafter "5SKF"). In order to compare both systems, the radiation dose was set to be equivalent; that is, the number of measurements acquired with each filter was set to be the same in both systems. For M=386 and P=450 in the 2 shot CSXI system, the number of angles in the 5SKF system was set to P=113 for Molybdenum and Tungsten and P=225 for the rest of the filters. In the ADMM algorithm the energy-binned CT image was represented on the sparse basis $\psi = \psi_{DCT} \otimes \psi_W$, where $\otimes$ is the Kronecker product, $\psi_{DCT}$ is the discrete cosine transform (DCT) basis in the energy domain, and $\psi_W$ is the 2D Haar wavelet basis in the spatial domain.

LS was used to obtain the energy-binned sinograms for the 5SKF system and then the energy-binned images are independently reconstructed using the 2D-FBP algorithm available in Matlab (ifanbeam function). The reconstructions of both systems were compared to the linear attenuation images, obtained from the NIST database, corresponding to the central energy in each energy bin, that is, 35 keV for k=1, 48 keV for k=2, 56 keV for k=3, and 64 keV for k=4. S was used to obtain the energy-binned sinograms for the 5SKF system and then the energy-binned images were independently reconstructed using the 2D-FBP algorithm available in Matlab (ifanbeam function). The reconstructions of both systems were compared to the linear attenuation images, obtained from the NIST database, corresponding to the central energy in each energy bin, that is, 35 keV for k=1, 48 keV for k=2, 56 keV for k=3, and 64 keV for k=4

The linear attenuation coefficients at the four energy bins, for the four pixels highlighted in FIG. 14 were determined for both the 5SKF and 2 shot CSXI systems as well as the reference images. The 4 pixels correspond to materials simulating lung, soft tissue, blood, and bone as detailed in Table 2. It should be noted that the 2 shot CSXI system provided a more accurate approximation of the spectral information of the target than the 5SKF system for all energy bins.

Additionally, reconstructions from both systems and the reference images at each energy bin were obtained. The peak signal to noise ratio (PSNR) was used to evaluate the reconstructions since it is suitable for comparing restoration results. For a scenario with an image I and a reconstruction R of size N×N it is defined as $$PSNR = 10\log_{10}\left(\frac{\text{Max}_I^2}{MSE}\right),$$

where is the maximum possible pixel value of the image I and MSE is the mean squared error given by $$MSE = \frac{1}{N^2}\sum_{i=0}^{N-1}\sum_{j=0}^{N-1}[I(i,j) - R(i,j)]^2.$$

It was observed that high-quality images at all energy bins were obtained using the CSXI system and the proposed algorithm. On the other hand, the results obtained using the 5SKF system presented numerous artifacts since FBP is not a suitable algorithm to solve the inverse problem when the number of view angles is limited. Furthermore, detector sub-sampling results in higher quality reconstructions compared to angle sub-sampling. Thus, the structure of the CSXI framework allowed for higher reconstruction quality as the sub-sampling is performed in the detectors instead of the view angles. Additionally, it was evident that the 5SKF system was not able to reconstruct all of the features in the original image—in this case, the ribs of the phantom—whereas the CSXI system was able to accurately reconstruct all of the features in the phantom.

Some filter elements were used more than once in the Ross pairs. For example, for the list of elements in Table 1, Ce was used for both k=1 and k=2, Dy was used for both k=2 and k=3, and Er is used for both k=3 and k=4. Thus, for a system with T>2 shots, instead of selecting a particular filter pair for each detector position j, a trio of elements could be assigned, such that one of the elements of the trio was used in more than one energy bin. This trio assignment can increase the sampling numbers in the sub-sampled sinograms, thus retaining more spectral information for each energy bin and improving the reconstruction performance especially when a large number of filters are used.

Additional experiments for a different phantom with more detailed features were performed for multiple values of P to evaluate the system at low-dose scenarios. For this experiment the target was 256×256, the number of detector elements per view was set to M=512, the source to detector distance and the source to target distance was set to 80 cm and 40 cm respectively and the detector length was set to 41.3 cm. Projections using the 5SKF system and the CSXI system for T=2 and T=3 shots were obtained. As in the previous scenario, the number of view angles P was set accordingly in each simulation so that the radiation dose was equivalent. For T=3, the elements of the K-edge coded apertures were chosen from Mo-Ce-Dy and Dy-Er-W for each detector position j, which resulted in energy-binned sinograms with 50% sub-sampling. In this simulation, the reconstructions of the 5SKF system were performed using TV regularization to exploit the sparsity of the target and counteract the limited view angle problem. It should be noted that the average PSNR of the reconstructions obtained with the CSXI system was higher for all the view angles for both T=2 and T=3 compared to the 5SKF system. Additionally, the radiation dose required by the CSXI system to obtain an average PSNR of 33.3 dB is approximately 30% of the radiation dose necessary in the 5SKF system to obtain a similar performance, which is of significant interest in medical applications. It was observed that there were more artifacts in the reconstructions obtained using the 5SKF system compared to the CSXI system even when using sparsity regularization constraints for both reconstructions. Furthermore, the PSNR improvement is up to 7 dB in the third and fourth energy bins.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed is:

1. A method for generating spectral computed tomography data for spectral X-ray image reconstruction, the method comprising the steps of:
   generating a plurality of X-ray beams;
   encoding the plurality of X-ray beams by transmitting the plurality of X-ray beams through a pixelated K-edge coded aperture structure;
   detecting the encoded plurality of X-ray beams; and
   reconstructing a spectral CT image from the encoded plurality of X-ray beams.

2. The method of claim 1, wherein the pixelated K-edge coded aperture structure delineates a plurality of openings, each of the plurality of openings containing at least one K-edge filter.

3. The method of claim 2, wherein a pair of K-edge filters contained within a corresponding pair of the plurality of openings form a pair of balanced K-edge filters.

4. The method of claim 3, wherein the pair of K-edge filters are formed of two materials having a difference in atomic numbers of 16 or less.

5. The method of claim 1, comprising transmitting the plurality of X-ray beams through a first blocking/unblocking structure for pixelating the plurality of X-rays beam and a second structure comprising at least one K-edge filter for filtering of the plurality of X-ray beams, wherein the first structure is separate from the second structure.

6. The method of claim 1, further comprising categorizing the encoded plurality of X-ray beams into energy bins.

7. The method of claim 1, wherein the restructuring of the spectral CT image includes using a quasi-monochromatic intensity.

8. The method of claim 1, wherein the encoding the plurality of X-ray beams comprises performing a first pass and a second pass on a target, and the restructuring of the spectral CT image of the target includes using a quasi-monochromatic intensity.

9. The method of claim 1, wherein the encoding of the plurality of X-ray beams comprises helically scanning the target.

10. The method of claim 1, further comprising rotating the target while maintaining a detector of the encoded plurality of X-ray beams and a generator of the plurality of X-ray beams stationary.

11. The method of claim 1, further comprising rotating a generator of the plurality of X-ray beams and rotating a detector of the encoded plurality of X-ray beams.

12. The method of claim 1, comprising generating the plurality of X-ray beams with a plurality of X-ray generators, each X-ray generator associated with a respective one of a plurality of pixelated K-edge coded aperture structures for encoding a respected X-ray beam.

13. A method for spectral X-ray tomography, the method comprising the steps of:
scanning a target with a plurality of X-ray beams during at least one pass of an X-ray beam generator with respect to the target;
encoding the plurality of X-ray beams during the at least one pass by transmitting the plurality of X-ray beams through a pixelated K-edge coded aperture structure, the pixelated K-edge coded aperture structure delineating a plurality of openings, the plurality of openings containing at least one pair of balanced K-edge filters;
detecting an intensity of the encoded plurality of X-ray beams from the at least one pass; and
reconstructing a spectral CT image of the target from the encoded plurality of X-ray beams.

14. The method of claim 13, wherein the restructuring of the spectral CT image of the target uses a quasi-monochromatic intensity.

15. The method of claim 14, wherein the at least one pass of the X-ray beam generator comprises a first pass and a second pass.

16. The method of claim 13, wherein the scanning comprises either rotating the target, while maintaining an X-ray detector for detecting the intensity of the encoded plurality of X-ray and the X-ray beam generator stationary or rotating the X-ray beam generator and rotating an X-ray detector for detecting the intensity of the encoded plurality of X-ray beams.

17. The method of claim 13, wherein the plurality of X-ray beams are generated with a plurality of X-ray generators, each X-ray generator associated with a respective pixelated K-edge coded aperture structure.

18. A system for generating a spectral computed tomography, the system comprising:
at least one X-ray generator configured to produce a plurality of X-ray beams;
at least one pixelated K-edge coded aperture structure delineating a plurality of openings, the plurality of openings associated with at least one K-edge filter, the plurality of openings configured to receive and transmit the plurality of X-ray beams with a difference in an energy band corresponding to a difference between K-edge values of a corresponding balanced pair of K-edge filters; and
at least one detector configured to detect the plurality of X-ray beams transmitted through the at least one pixelated K-edge coded aperture structure.

19. The system of claim 18, wherein the at least one pixelated K-edge aperture has a non-randomized pattern and is configured to encode the plurality of X-ray beams transmitted through the at least one pixelated K-edge coded aperture structure with the non-randomized pattern.

20. The system of claim 18, wherein each of the plurality of openings of the at least one pixelated K-edge aperture is arranged with respect to other openings to spatially encode the plurality of X-ray beams transmitted through the plurality of openings of the at least one pixelated K-edge coded aperture structure.

21. The system of claim 18, wherein the at least one detector is a line detector or a two dimensional detector.

22. The system of claim 18, wherein the detector elements are positioned on a semicircular (arch) geometry.

23. The system of claim 18, further comprising a plurality of X-ray generators, each X-ray generator associated with a respective pixelated K-edge coded aperture structure.

24. The system of claim 18, wherein a geometry of the system corresponds to a tomosynthesis system.

25. The system of claim 18, wherein the at least one X-ray generators and the at least one detector are rotatable.

26. The system of claim 18, further comprising a patient positioning system configured for positioning a target.

* * * * *